US007615612B2

(12) United States Patent
Carroll et al.

(10) Patent No.: US 7,615,612 B2
(45) Date of Patent: Nov. 10, 2009

(54) POLYPEPTIDE

(75) Inventors: Miles W. Carroll, Oxford (GB); Kevin A. Myers, Oxford (GB)

(73) Assignee: Oxford Biomedica (UK) Limited, Oxford (GB)

( * ) Notice: Subject to any disclaimer, the term of this patent is extended or adjusted under 35 U.S.C. 154(b) by 64 days.

(21) Appl. No.: 11/686,793

(22) Filed: Mar. 15, 2007

(65) Prior Publication Data

US 2007/0298055 A1 Dec. 27, 2007

Related U.S. Application Data

(63) Continuation of application No. 11/286,056, filed on Nov. 22, 2005, which is a continuation of application No. 09/533,798, filed on Mar. 24, 2000, now Pat. No. 7,148,035, and a continuation of application No. PCT/GB99/03859, filed on Nov. 18, 1999.

(60) Provisional application No. 60/126,188, filed on Mar. 25, 1999, provisional application No. 60/126,187, filed on Mar. 25, 1999.

(30) Foreign Application Priority Data

Nov. 18, 1998 (GB) ............................... 9825303.2
Jan. 27, 1999 (GB) ............................... 9901739.4
Jul. 30, 1999 (GB) ............................... 9917995.4

(51) Int. Cl.
*C07K 14/00* (2006.01)
(52) U.S. Cl. .................................................. 530/350
(58) Field of Classification Search ....................... None
See application file for complete search history.

(56) References Cited

U.S. PATENT DOCUMENTS

| 4,558,035 A | 12/1985 | Johnson |
| 5,118,672 A | 6/1992 | Schinazi et al. |
| 5,869,053 A | 2/1999 | Stern et al. |

FOREIGN PATENT DOCUMENTS

| EP | 0110385 A2 | 6/1984 |
| EP | 0198328 A2 | 10/1986 |
| WO | WO89/07947 A1 | 9/1989 |
| WO | WO92/03568 A1 | 3/1992 |
| WO | WO97/19183 A2 | 5/1997 |
| WO | WO99/15683 A1 | 4/1999 |
| WO | WO99/15684 A2 | 4/1999 |

OTHER PUBLICATIONS

Ezzell (J. NIH Res, 1995, 7:46-49).*
Spitler (Cancer Biotherapy, 1995, 10:1-3.*
Boon (Adv Can Res, 1992, 58:177-210).*
DeGruijl et al (Nature Medicine, 5410): 1124-1125, Oct. 1999).*
Bodey et al (Anticancer Research. 20:2665-2676; 2000).*
Gaiger et al (Blood, vol. 96, No. 4, Aug. 2000, pp. 1480-1489).*

Guschlbauer, et al. "Poly-2'-deoxy-2'-fluoro-cytidylic acid: enzymatic synthesis, spectroscopic characterization and interaction with poly-inosinic acid", *Nucleic Acids Res.* (1977) 4:1933.
Schibahara, et al. "Site-directed cleavage of RNA", *Nucleic Acids Res.* (1987) 15:4403.
Gershon, et al. "The nucleotide sequence around the capripoxvirus thymidine kinase gene reveals a gene shared specifically with leporipoxvirus", *J. Gen. Virol*, (1989) 70:525.
Weir, et al. "Nucleotide sequence of the vaccinia virus thymidine kinase gene and the nature of spontaneous frameshift mutations", *J. Virol.*(1983) 46:530.
Esposito, et al. "Nucleotide sequence of the thymidine kinase gene region of monkeypox and variola viruses", *Virology* (1984) 135:561.
Kilpatrick, et al. "Cloning and physical mapping of yada monkey tumor virus DNA" *Virology* (1985) 143:399.
Binns, et al. "Comparison of a conserved region in fowlpox virus and vaccinia virus gnomes and the translocation of the fowlpox virus thymidine kinase gene", *J. Gen Virol* (1988) 69:1275.
Schnitzlein, et al. "A rapid method for identifying the thymidine kinase genes of avipoxviruses", *J. Virological Method* (1988) 23:341.
Fathi, et al. "Efficient targeted insertion of an unselected marker into the vaccinia virus genome", *Virology* (1986) 97:105.
Graham, et al. "A new technique for the assay of infectivity of human adenovirus 5 DNA", *Virol.* (1973) 52:456-467.
Straibinger, et al. "Liposomes as carriers for intracellular delivery of nucleic acids", *Methods in Enzymology*, (1983) 101:512-527.
Studier, et al. "Use of T7 RNA polymerase to direct expression of cloned genes", *Methods in Enzymol.* (1990) 185:60-89.
Matthias, et al. "Eukaryotic expression vectors for the analysis of mutant proteins", *NAR* (1989) 17:6418.
Wootton & Federhen, "Statistics of local complexity in amino acid sequences and sequence databases", *Computers and Chemistry* (1993) 17:149-163.
Myers, et al. "Isolation of a cDNA encoding 5T4 oncofetal trophoblast glycoprotein", *J. Biol. Chem.* (1994) 169:9319-9324.
Starzynska, et al. "The expression of 5T4 antigen in colorectal and gastic carcinoma", *Br. J. Cancer* (1992) 66(5):867-869.
Starzynska, et al. "Prognostic significance of 5T4 oncofetal antigen expression in colorectal" *Br. J. Cancer* (1994) 69(5):899-902.
Hobbs, et al. "Polynucleotides containing 2'-amino-2'-deoxyribose and 2'-azido-2'-deoxyribose", *Biochemistry* (1973) 12:5138.
Starzynska, et al. "5T4 oncofetal antigen in gastric carcinoma and its clinical significance", *Eur J. Gastroenterol Hepatol* (1998) 10(6)479-484.

(Continued)

*Primary Examiner*—Christopher H Yaen
(74) *Attorney, Agent, or Firm*—Marshall, Gerstein & Borun LLP

(57) ABSTRACT

The present invention provides 5T4 tumour-associated antigen (TAA) for use in a method of immunotherapy of tumours. The invention also relates to a recombinant poxvirus vector from which at least one immune evasion gene has been deleted, which comprises a nucleic acid sequence encoding a 5T4 TAA and the use thereof in vaccinating against and in treating tumours.

16 Claims, 14 Drawing Sheets

OTHER PUBLICATIONS

Carsberg, et al. "Metastasis-associated 5T4 antigen disrupts cell-cell contacts and induces cellular motility in epithelial cells", *Int. J. Cancer* (1996) 68(1):84-92..

Yewdell, et al. "TAP-independent delivery of antigenic peptides to the endoplasmic reticulum: therapeutic potential and insights into TAP-dependent antigen processing", *J. Immunotherapy* (1998) 21:127-31.

Calvert, et al. "Fowlpox virus recombinants expressing the envelope glycoprotein of an avian reticuloendotheliosis retrovirus induce neutralizing antibodies and reduce viremia in chickens", *J. of Virol.* (1993) 67:3069-3076.

Carroll, et al. "Construction and characterization of a triple-recombinant vaccinia virus encoding B7-1, interleukin 12, and a model tumor antigen", *J. Natl. Cancer Inst.* (1998) 90(24):1881-1887.

Carroll, et al. "Two bright new faces in gene therapy", *Nature Biotechnology* (1996) 14:556.

Pieken, et al. "Kinetic characterization of ribonuclease-resistant 2'-modified hammerhead ribozymes", *Science* (1991) 253:314-317.

Parker, et al. "Scheme for ranking potential HLA-A2 binding peptides based on independent binding of individual peptide side-chains", *J. Immunol.* (1994) 152:163-175.

Fu, et al. "An endoplasmic reticulum-targeting signal sequence enhances the immunogenicity of an immunorecessive simian virus 40 large T antigen cytotoxic T-lymphocyte epitope", *J. Virol.* (1998) 72:1469-81.

Schodel, et al. "Hepatitis B virus core and e antigen: immune recognition and use as a vaccine carrier moiety", *Intervirology* (1996) 39:104-10.

Wolff and Trubetskoy "The cambrian period of nonviral gene delivery", *Nature Biotechnology* (1998), 16:421-423.

Taylor, et al. "Biological and immunogenic properties of a canarypox-rabies recombinant, ALVAC-RG (vCP65) in non-avian species", *Vaccine* (1995) 13:539-549.

Stannard, et al. "Evidence for incomplete replication of a penquin poxvirus in cells of mammalian origin" , *J. Gen. Virol.* (1998) 79:1637-46.

Mackett, et al. "Vaccinia virus: a selectable eukaryotic cloning and expression vector", *PNAS* (1982) 79:7415-7419.

Upton, et al. "Identification and nucleotide sequence of the thymidine kinase gene of shope fibroma virus", *J. Virology* (1986) 60:920.

Boyle, et al. "Fowlpox virus thymidine kinase: nucleotide sequence and relationships to other thymidine kinase", *Virology* (1987) 156:355-365.

Lewis, et al. "Human immunodeficiency virus infection of cells arrested in the cell cycle" *EMBO J.* (1992) 11:3053-3058.

Lewis and Emerman, "Passage through mitosis is required for oncoretroviruses but not for the human immunodeficiency virus", *J. Virol.* (1994) 68:510-516.

Mackett, et al. "General method for production and selection of infectious vaccinia virus recombinants expressing foreign genes", *J. Virol.* (1984) 49:857-864.

Hruby, et al. "Fine structure analysis and nucleotide sequence of the vaccinia virus thymidine kinase gene", *PNAS* (1983) 80:3411-3415.

Lytvyn, et al. "Comparison of the thymidine dinase genes from three entompoxiruses", *J. Gen Virol,* (1992) 73:3235-3240.

Smith, et al. "Vaccinia virus immune evasion", *Immunol Rev.* (1997) 159:137-154.

Jenkins, et al. "Formation of lentivirus particles by mammalian cells infected with recombinant fowlpox virus", *AIDS Research and Human Retroviruses* (1991) 7:991-998.

Taylor, et al. "Recombinant fowlpox virus inducing protective immunity in non-avian species", *Vaccine* (1988) 6:497-503.

Sphener, et al. "Insertion of the fusion gene from Newcastle disease virus into a non-essential region in the terminal repeats of fowlpox virus and demonstration of protective immunity induced by the recombinant", *J. Gen. Virol.* (1990) 71:621-628.

Nakano, et al. "Molecular genetics of vaccinia virus: demonstration of marker rescue", *Proc. Natl. Acad. Sci. USA* (1982) 79:1593-1596.

Chakrabarti, et al. "Vaccinia virus expression vector: coexpression of β-galactosidase provices visual screening of recombinant virus plaques", *Mol. Cell. Biol.* (1985) 3403-3409.

Wigler, et al. "Transformation of mammalian cells with genes from prokaryotes and eukaryotes", *Cell*, (1979) 777-785.

Graessmann, et al. "Microinjection of tissue culture cells", *Meth. Enzymology* (1983) 101:482-492.

Franke, et al. "Neomycin resistance as a dominant selectable marker for selection and isolation of vaccinia virus recombinants", *Mol. Cell. Biol.* (1985) 1918-1924.

Altenburger, W., et al. "Partial deletion of the human host range gene in the attenuated vaccinia virus MVA" *Arch. Virol.* (1989) 105:15-27.

Neumann, et al. "Gene transfer into mouse lyoma cell by electroporation in high electric fields", *EMBO J.* (1982) 1:841-845.

Schaffner, "Direct transfer of cloned genes from bacteria to mammalian cells", *Proc. Natl. Acad. Sci. USA* (1980) 77:2163-2167.

Nestle, F.O., et al. Vaccination of melanoma patients with peptide-or tumor lysate-pulsed dendritic cells', *Nat. Med.* (1998) 4(3):328-32.

Altschul, et al. "Issues in searching molecular sequence database" *Nature Genetics* (1994) 6:119-129.

Carroll, et al. "Host range and cytopathogenicity of the highly attenuated MVA strain of vaccinia virus: propagation and generation of recombinant viruses in a nonhuman mammalian cell line", *Virology* (1997) 238:198-211.

Kim, C. J., et al. "Dendritic cell infected with poxviruses encoding Mart-1/melan a sensitive T lymphocytes in vitro", *J. Immunother* (1997) 20(4):276-86.

Schneider, et al. "Enhanced immunogenicity for CD8 + T cell induction and complete protective efficacy of malaria DNA vaccination by boosting with modified vaccinia virus Ankara", *Nat. Med.* (1998) 4:397-402.

Chakrabarti, et al. "Compact, synthetic, vaccinia virus early/late promoter for protein expression" *Biotechniques* (1997) 23:1094-1097.

Wyatt, et al. "Development of replication-deficient recombinant vaccinia virus vaccine effective against parainfluenza virus 3 infection in an animal model", *Vaccine* (1996) 14:1451-1458.

Sutter, et al. "A recombinant vector derived from the host range-restricted and highly attenuated MVA strain of vaccinia virus stimulates protective immunity in mice to influenza virus", *Vaccine* (1994) 12:1032-1040.

Carroll, et al. "*E. coli* β-glucuronidase (GUS) as a marker for recombinant vaccinia viruses", *Biotechniques* (1995) 19:352-355.

Hirsch, et al. "Patterns of viral replication correlate with outcome in simian immunodeficiency virus (SIV)-infected macaques: effect of prior immunization with a trivalent SIV vaccine in modified vaccinia virus Ankara", *J. Virol.* (1996) 70:3741-3752.

Sutter, et al. "Nonreplicating vaccinia vector efficiently expresses recombinant genes",*Proc. Natl. Acad. Sci. USA*, (1992) 89:10847-10851.

Bronte, et al. "Antigen expression by dendritic cells correlates with the therapeutic effectiveness of a model recombinant poxvirus tumor vaccine", *Proc. Natl. Acad. Sci. USA* (1997) 94(7):3183-3188.

Wyatt, et al. "Replication-deficient vaccinia virus encoding bacteriophage T7 RNA polymerase for transient gene expression in mammalian cells", *Virology* (1995) 210:202-205.

Carroll, et al. "Highly attenuated modified vaccinia virus Ankara (MVA) as an effective recombinant vector: a Murine tumor model", *Vaccine* (1997) 15:387-394.

Sutter, et al. "Non-replication vaccinia vector efficiently expresses bacteriophage T7 RNA polymerase", *FEBS lett.* (1995) 371:9-12.

Overwijk, et al. "gp100/pmel 17 is a murine tumor rejection antigen induction of Self-reactive, tumoricidal T cells using high-affinity, altered peptide ligand", *J. Exp. Med.* (1998) 188:277-286.

Hole, N., et al. "Isolation and characterization of 5T4, a tumor-associated antigen", *Int. J. Cancer* (1990) 45(1):179-184.

Correale, Pierpaolo, et al. "Generation of Human Cytolytic T Lymphocyte Lines Directed Against Prostate-Specific Antigen (PSA) Employing a PSA Oligoepitope Peptide", *The Journal of Immunology* (1998) 161:3186-3194.

Hodge, James W., et al. "A Recombinant Vaccinia Virus Expressing Human Prostate-Specific Antigen (PSA): Safety and Immunogenicity in a Non-Human Primate", *Int. J. Cancer* (1995) 63:213-237.

Hole, N., et al. "A 72 kD trophoblast glycoprotein defined by a monoclonal antibody", *Br. J. Cancer* (1998) 57:239-246.

Irvine, Kari R., et al. "Synthetic Olignoucleotide Expressed by a Recombinant Vaccinia Virus Elicits Therapeutic CTL", *The Journal of Immunology* (1995) 154:4651-4657.

Jackson, Ronald J., et al. "Infertility in Mice Induced by a Recombinant Ectromelia Virus Expressing Mouse Zona Pellucida Glycoprotein 3", *Biology of Reproduction* (1998) 58:152-159.

Kass, Erik, et al. "Induction of Protective Host Immunity to Carcinoembryonic Antigen (CEA), a Self-Antigen in CEA Transgenic Mice, by Immunizing with a Recombinant Vaccinia-CEA Virus", *Cancer Research* (1999) 59:676-683.

Rosato, Antonio, et al. "CTL Response and Protection Against P815 Tumor Challenge in Mice Immunized with DNA Expressing the Tumor-Specific Antigen P815A", *Human Gene Therapy* (1997) 8:1451-1458.

Sanda, Martin G., et al. "Recombinant Vaccinia-PSA (Prostvac) Can Induce a Prostate-Specific Immune Response in Androgen-Modulated Human Prostate Cancer", *Urology* (1999) 53:260-266.

Southall, P.J., et al. "Immunohistological distribution of 5T4 antigen in normal and malignant tissues", *Br. J. Cancer* (1990) 61:89-95.

Tsang, Kwong Y., et al. "Generation of Human Cytotoxic T Cells Specific for Human Carcinoembryonic Antigen Epitopes From Patients Immunized With Recombinant Vaccinia-CEA Vaccine", *J. Natl. Cancer Inst.* (1995) 87(13):982-990.

Wang, Rong-Fu "Tumor Antigens Discovery: Perspectives for Cancer Therapy", *Molecular Medicine* (1997) 3(11):716-731.

Perkins, David L., et al. "Immunodominance: Intramolecular Competition Between T-Cell Epitopes", *J. Immunol.* (1997) 146(7):2137-2144.

Theobald, Matthias, et al. "The Sequence Alteration Associated with a Mutational Hotspot in p53 Protects Cells from Lysis by Cytotoxic T Lymphocytes Specific for a Flanking Peptide Epitope", *J. Exp. Med.* (1998) 188(6):1017-1028.

Gileadi, Uzi, et al. "Effect of epitope flanking residues on the presentation of N-terminal cytotoxic T lymphocyte epitopes", *Eur. J. Immunol.* (1999) 29:2213-2222.

Engelhard, Victor H. "Structure of peptides associated with MHC class 1 molecules", *Current Opinion in Immunology* (1994) 6:13-23.

Eisenlohr, Laurence C., et al. "Flanking Sequences Influence the Presentation of an Endogenously Synthesized Peptide to Cytotoxic T Lymphocytes", *J. Exp. Med.* (1992) 175:481-487.

Shastri, Nilbah, et al. "Presentation of Endogenous Peptide/MHC Class I Complexes is Profoundly Influenced by Specific C-Terminal Flanking Residues", *J. Immunol.* (1995) 155:4339-4346.

Bergmann, Cornelia C., et al. "Differential Effects of Flanking Residues on Presentation of Epitopes from Chimeric Peptides", *J. Virol.* (1994) 68(8):5306-5310.

Wang, Yusheng, et al. "Silencing of Immunodominant Epitopes by Contiguous Sequences in Complex Synthetic Peptides", *Cell Immunol.* (1992) 143:284-297.

Celis, Esteban, et al. "Identification of Potential CTL Epitopes of Tumor-Associated Antigen Mage-1 for Five Common HLA-A Alleles", *Molec.Immunol.* (1994) 31:(18):1423-1430.

Guo, Hwai-Chen, et al. "Different length peptides bind to HLA-Aw68 similarity at their ends but bulge out in the middle", *Nature* (1992) 360:364-366.

Ochoa-Garay, Jorge, et al. "The Ability of Peptides to Induce Cytotoxic T Cells In Vitro Does Not Strongly Correlate With Their Affinity for H-2L$^d$ Molecule: Implications for Vaccine Design and Immunotherapy", *Molec. Immunol.* (1997) 34(3):273-281.

Chaux, Pascal, et al. "Estimation of the Frequencies of Anti-Mage-3 Cytolytic T-Lymphocyte Precursors in Blood From Individuals Without Cancer", *Int. J. Cancer* (1998) 77:538-542.

GenEmbl Accession No. Z29083 (1998).

Stern, Peter, et al. "Characterization of the Human Trophoblast-Leukocyte Antigenic Molecules Defined by a Monoclonal Antibody", *The Journal of Immunology* (1986) 137(5):1604-1609.

Johnson, P.M., et al. Human Trophoblast-Specific Surface Antigens Identified Using Monoclonal Antibodies', *American Journal of Reproductive Immunology* (1981) 1:246-254.

Rettig, Wolfgang J., et al. "Cell Surface Antigens of Human Trophoblast and Choriocarcinoma Defined by Monoclonal Antibodies", *Int. J. Cancer* (1985) 35:469-475.

Hole, M., et al. "Trophoblast-Specific Glycoprotein Defied by Monoclonal Antibody 5T4", *British Society for Immunology & British Transplantation Society 1986 Joint Annual Meeting*. Nov. 12-14, 1986, abstract 66.

Stern, P.L. et al. "Molecular Characterisation of Human Terato-Carcinoma-Trophoblast Cell Surface Antigens", *J. Repro. Immun.*, Supp: 6 (Jun. 1986).

Anderson, Deborah J., et al. Monoclonal antibodies to human trophoblast and sperm antigens: Report of two WHO sponsored workshops, Jun. 30, 1986—Toronto, Canada *J. Repro. Immun.* (1987) 10:231-257.

Cho, S.-W., et al. "Characterization of three monoclonal antibodies to membrane co-factor protein (MCP) of the complement system and quantification of MCP by raidioassay", *Clin. Exp. Immunol.* (1991) 83:257-261.

Purcell, D.F.J., et al. "The human cell-surface glycoproteins HuLym5, membrane co-factor protein (MCP) of the complement system, and trophoblast leucocyte-common (TLX) antigen, are CD46", *Immunology* (1990) 70:155-161.

Coulie P. "Human Tumor Antigens Recognized by Cytolytic T Lymphocytes", Chapter 5, pp. 95-125, *Tumor Immunology*, Eds. Dagleish & Browning, Cambridge University Press 1996.

Rosenkrantz, K., et al. "Generation and regulation of autocytotoxicity in mixed lymphocyte cultures: Evidence for active suppression of autocytotoxic cells", *PNAS* (1985) 82:4508-4512.

Stavely-O'Carroll, et al. "Induction of antigen-specific T cell energy: An early event in the course of tumor progression", *PNAS* (1988) 95:1178-1183.

Manson, L, et al. "Short Analytical Review—Anti-tumor Immune Responses of the Tumor Bearing Host: The Case for Antibody-Mediated Immunologic Enhancement", *Clinical Immunology & Immunopathology* (1994) 72(1):1-8.

Ganss, R., et al. "Tumor Microenvironment Can Restrict the Effectiveness of Activated Antitumor Lymphocytes", *Cancer Research* (1988) 58:4673-4681.

Berd, D. "Cancer Vaccines: Reborn or Just Recycled?", *Seminars in Oncology* (1998) 25(6):605-610.

Hersey, P., et al. "Impediments to Successful Immunotherapy", *Pharmcol. Ther.* (1999) 81(2):111-119.

Takahashi, K., et al. "Escape Mechanisms of Melanoma From Immune System By Soluble Melanoma Antigen", *The Journal of Immunology* (1988) 140(9):3244-3248.

Janeway & Travers, *Immunobiology: The Immune System in Health and Disease*, Third edition, Current Biology Ltd./Garland Publishing Inc. (1997).

Amato, R., et al. "Phase II Trial to Assess the Activity of MVA 5T4 (Trovax®) alone versus MVA 5T4 plus Granulocyte Macrophage Colony-Stimulating Factor (GM-CSF) in Patients (pts) with Progressive Hormone Refractory Prostate Cancer (HRPC), Abstract, 18th EORTC-NCI-AACR Symposium on Molecular Targets and Cancer Therapeutics", Nov 7-10, 2006, Prague, Czech Republic.

Amato, R., et al. "Activity of MVA 5T4 alone or in Combination with either Interleukin-2 (IL-2), Interferon-α (IFN), or Sunitinib in Patients (Pts) with Metastatic Renal Cell Cancer (MRCC), Abstract, 18th EORTC-NCI-AACR Symposium on Molecular Targets and Cancer Therapeutics", Nov. 7-10, 2006, Prague, Czech Republic.

Sykulev, Y., et al. "Evidence that a Single Peptide-MHC Complex on a Target Cell Can Elicit a Cytolytic T Cell Response", *Immunity* (1996) 4:565-571.

Oxford BioMedica announces data safety monitoring board recommendation to continue TroVex® phase III trist study. Achievement triggers ∈10 million milestone payment from Sanofi-Aventis. News 2008/OB/04, Feb. 20, 2008.

Oxford BioMedica Completes patient recruitment for phase III Trist study of TroVax® in renal cancer. New 2008/OB/06, Mar. 10, 2008.

Amato et al., Vaccination of prostate cancer patients with modified vaccinia Ankara delivering the tumor antigen 5T4 (TroVax®): a phase II trail. TAT Meeting 2008, 2008/OB/09 abstract, Oxford BioMedica Ltd, Oxford, U.K. Mar. 18, 2008.

Oxford BioMedica Report encouraging new phase II trail results with TroVax® in prostate cancer. News 2008/0B/09, Mar. 25, 2008.

Oxford BioMedica announces TroVex® phase II trail results in renal cancer to be presented at ASCO. News 2008/OB/14, May 16, 2008.

Sanofi-Aventis and Oxford BioMedica report encouraging TroVax® phase II trial results in metastatic renal cancer. News 2008/OB/17, Jun. 2, 2008.

Oxford BioMedica announces data safety monitoring board recommendation for TroVax® phase III TRIST study. News 2008/OB/21. Jul. 11, 2008.

Oxford BioMedica received commitment or independent phase III trail of TroVax® in adjuvant colorectal cancer. News 2008/OB/22, Jul 14, 2008.

Oxford BioMedica reports further data from interim review of TroVax® phase III TRIST study. News 2008/OB/23, Jul. 15, 2008.

McDonald, Letter to investigator, TV3/001/06: An international, randomized, double blind, placebo controlled, parallel group study to investigate whether TroVax®, added to first-line standard of care therapy, prolongs the survival of patients with locally advanced or metastatic clear cell renal adenocarcinoma (TRIST) Jul. 15, 2008.

* cited by examiner

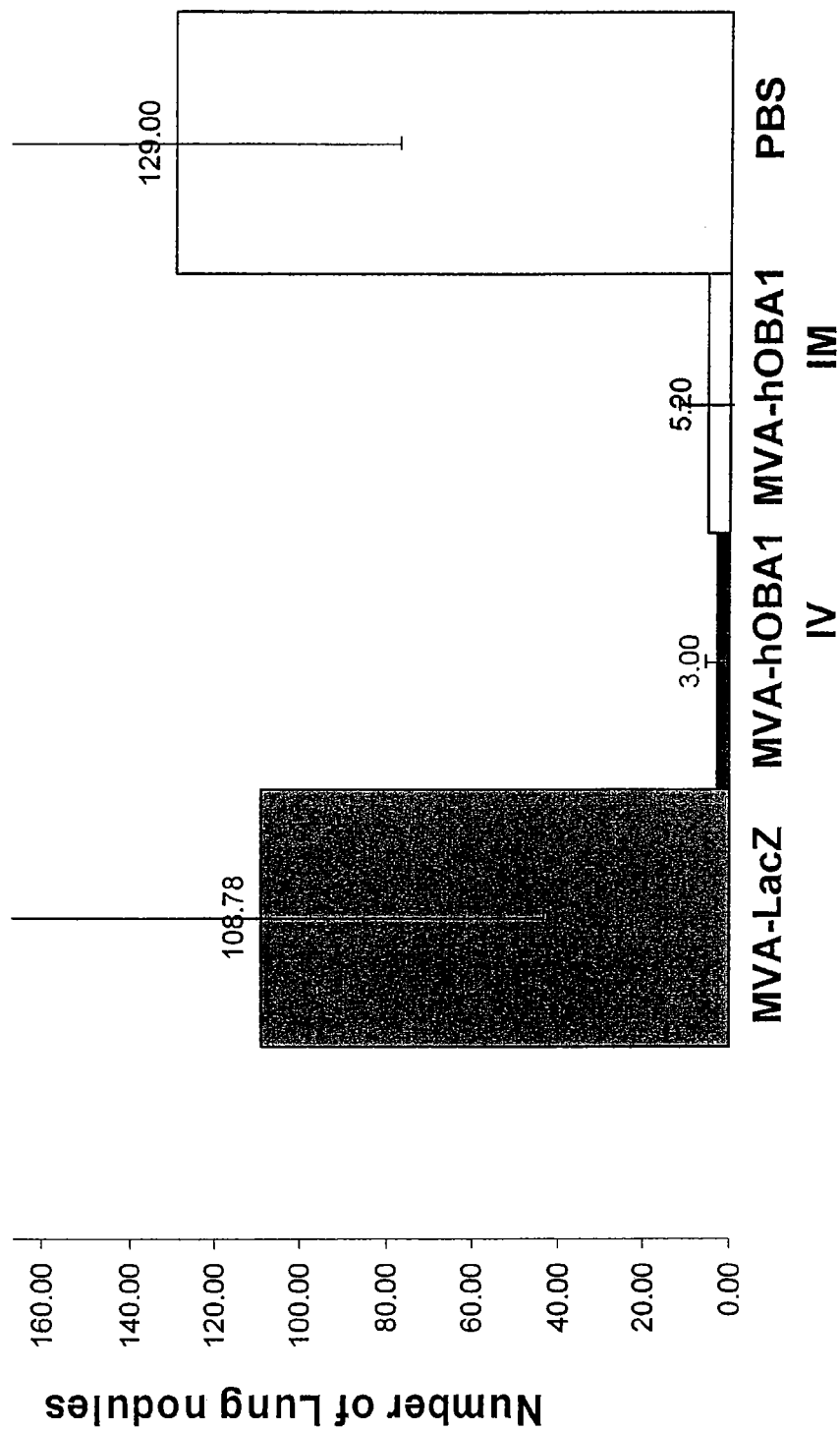

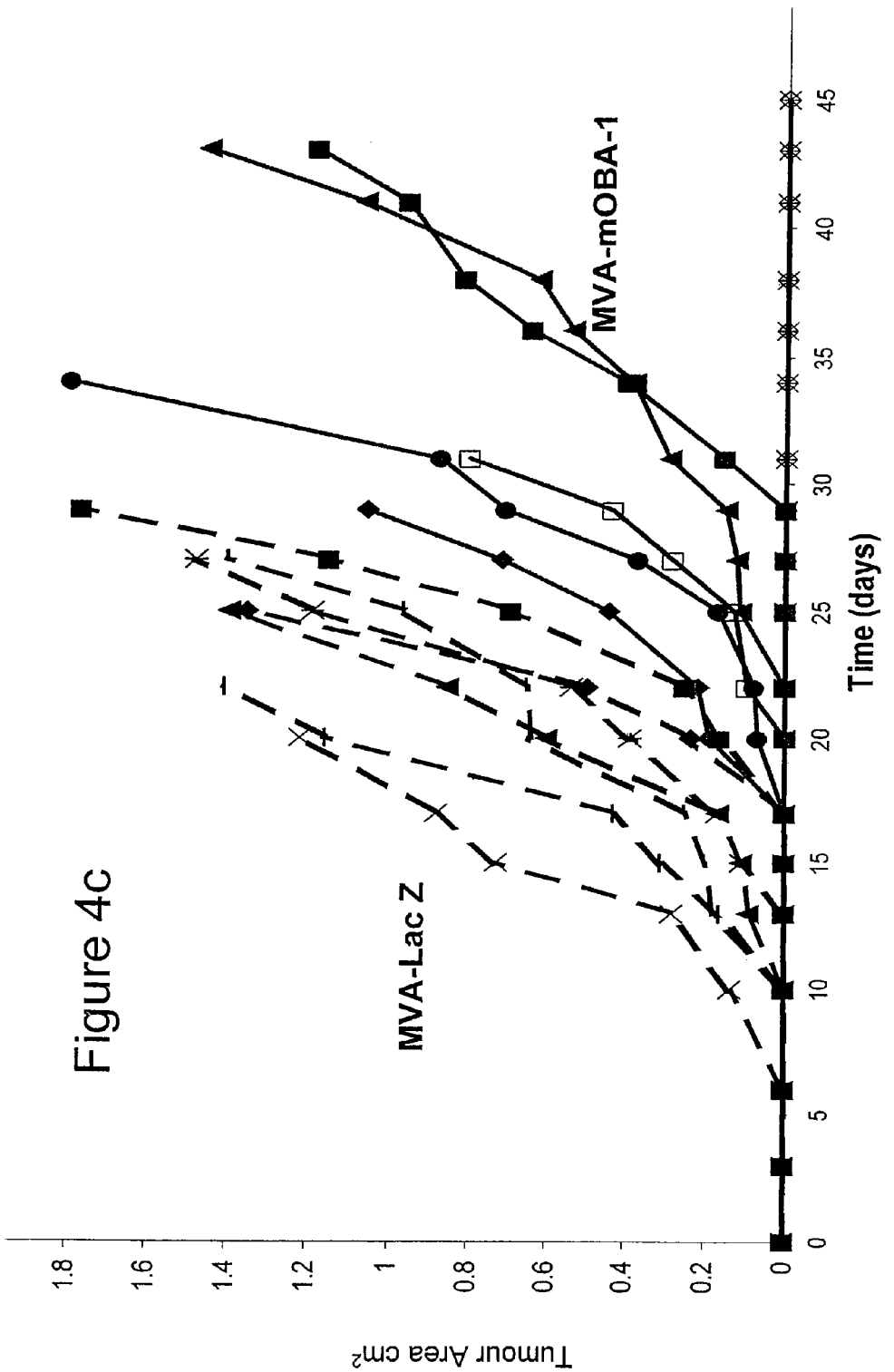

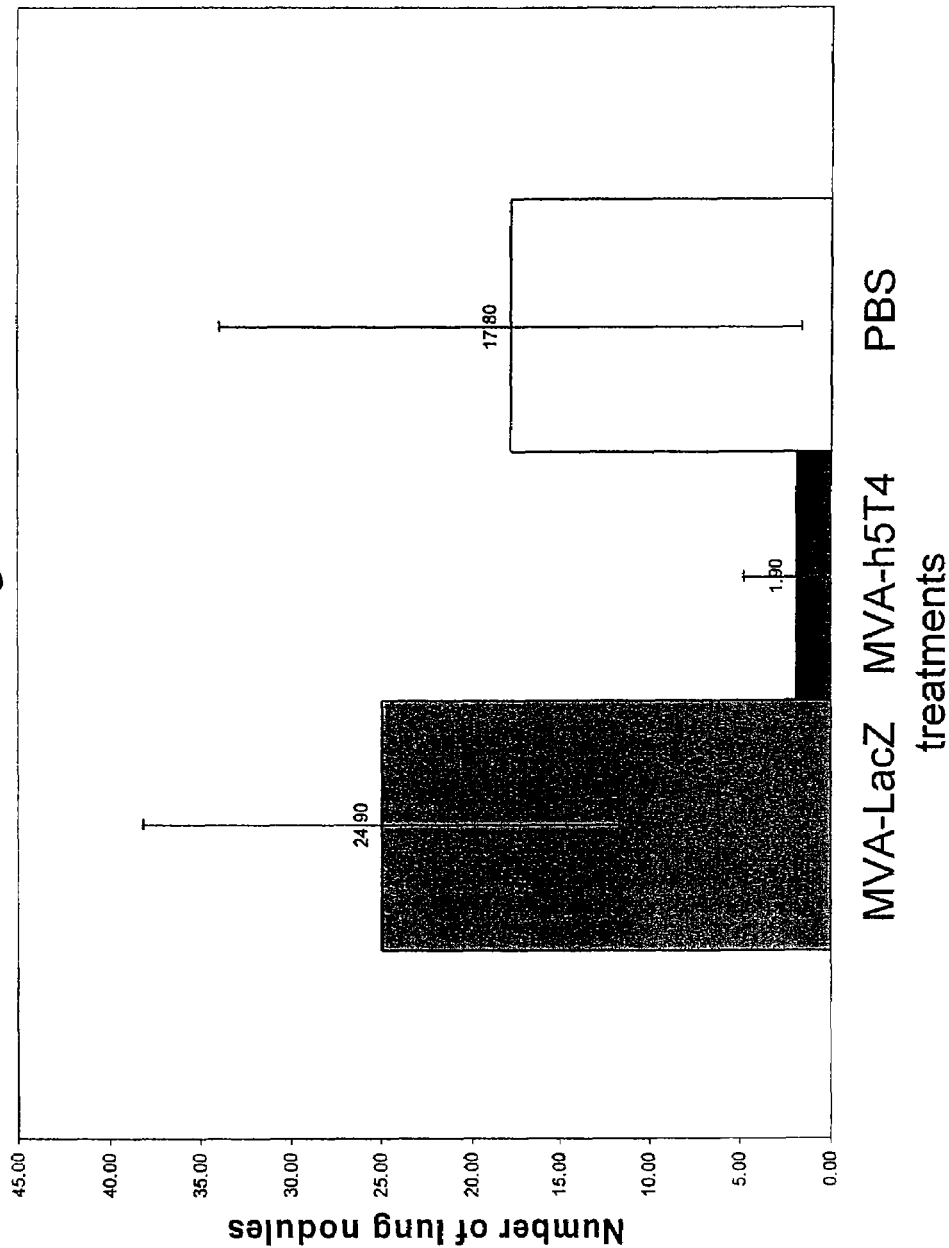

POLYPEPTIDE

This application is a continuation of U.S. patent application Ser. No. 11/286,056, filed Nov. 22, 2005, which is a continuation of U.S. patent application Ser. No. 09/533,798, filed Mar. 24, 2000, now U.S. Pat. No. 7,148,035, which claims benefit of priority from U.S. Provisional Patent Applications 60/126,187, filed Mar. 25, 1999, and 60/126,188, filed Mar. 25, 1999, as well as PCT/GB99/03859, filed Nov. 18, 1999 and designating the U.S., which claims benefit of priority from GB 9825303.2, filed Nov. 18, 1998, GB 9901739.4, filed Jan. 27, 1999, and GB 9917995.4, filed Jul. 30, 1999; all applications are hereby incorporated by reference in their entireties as if fully set forth.

FIELD OF THE INVENTION

The present invention relates to a tumour-associated antigen (TAA) useful for eliciting an anti-tumour immunotherapeutic response in subjects. In particular, the invention relates to 5T4 antigen and its use in immunotherapy.

BACKGROUND TO THE INVENTION

A number of oncofoetal or tumour-associated antigens (TAAs) have been identified and characterised in human and animal tumours. In general, TAAs are antigens expressed during foetal development which are downregulated in adult cells, and are thus normally absent or present only at very low levels in adults. Tumour cells have been observed to resume expression of TAAs, and the application of TAAs for tumour diagnosis, targeting and immunotherapy has therefore been suggested.

In particular, the recent cloning of tumour antigens recognised by T cells has caused considerable interest in the development of antigen specific cancer vaccines. However, many tumour associated antigens are non-mutated, poorly immunogenic tissue differentiation antigens. Their weak immunogenicity may be due to self tolerance. Thus they are rarely indicated as antigenic peptides suitable for raising an immune response.

Notwithstanding this, some tumour associated antigens are found to be regularly associated with tumours in a large number of individuals. Such antigens are especially attractive candidates for use in vaccines. They include the melanoma differentiation antigens (MDA), melanoma antigens which are recognised by T lymphocytes as well as several proteins in the MAGE family. However, as indicated by results from clinical trials obtained to date, inducing therapeutic T cells to these antigens has proved extremely difficult. One reason for the apparent hyporesponsiveness of the human immune system to many tumour antigens may be that they are normal, non-mutated self antigens, expressed on normal tissues as well as on tumour cells. The immune system is not able to differentiate the tumour antigen on a tumour cell from ordinary, self proteins.

A major barrier to the application of tumour immunotherapy approaches using non-mutated self cellular antigens is thus apparently the breaking of tolerance to such an antigen. For example, a murine zona pellucida antigen expressed by a murine poxvirus recombinant was able to induce infertility in mice. These data indicate that though the breaking of tolerance using recombinant pox viruses expressing self antigens is possible, there is still a requirement to optimise their efficacy such that the active treatment of established tumours becomes possible.

The TAA 5T4 (see WO 89/07947) has been extensively characterised. It is a 72 kDa glycoprotein expressed widely in carcinomas, but having a highly restricted expression pattern in normal adult tissues (see Table 1). It appears to be strongly correlated to metastasis in colorectal and gastric cancer. The full nucleic acid sequence of human 5T4 is known (Myers et al., 1994 J Biol Chem 169: 9319-24).

TABLE 1

Distribution of Human 5T4

| Tumour Type | 5T4 Frequency (%) |
|---|---|
| Breast | 84 |
| Ovarian | 71 |
| Gastric | 74 |
| Colorectal | 85 |

(Starzynska et al., Eur J Gastroenterol Hepatol June 1998; 10(6):479-84; Starzynska et al., Br. J Cancer May 1994;69 (5):899-902; Starzynska et al., Br J Cancer November 1992; 66(5):867-9)

Although 5T4 has been proposed as a marker, with possible mechanistic involvement, for tumour progression and metastasis potential (Carsberg et al., (1996) Int J Cancer Sep. 27, 1996;68(1):84-92), 5T4 has not been proposed for use as an immunotherapeutic agent. The breaking of immune tolerance to 5T4, which is itself expressed in a restricted manner in adult tissues, has not been demonstrated. Thus, it could not be predicted whether 5T4 could prove to be an effective antigen for immunotherapy against cancer.

SUMMARY OF THE INVENTION

If a successful therapeutic outcome is to be achieved, an immunotherapeutic approach to cancer treatment depends on a number of factors. These include the ability to elicit a cytotoxic T-lymphocyte (CTL) response, the ability to elicit an antibody response and, importantly, the ability to break immune tolerance in a subject. It has now been demonstrated that immunisation of subjects with 5T4 results in a successful immunotherapeutic response as judged by the above. In particular, immunisation with 5T4 has been shown to elicit an antibody response.

Accordingly, the present invention provides a viral vector expressing a nucleic acid encoding 5T4 antigen.

Expression of 5T4 antigen in a subject is effective in eliciting an immunotherapeutic anti-tumour response. Preferably, the viral vector favours CTL responses to expressed antigens, and is advantageously a poxvirus vector, such as a vaccinia virus vector. Further vectors, both viral and non-viral, which are suitable for delivering 5T4 antigen are described below.

As used herein, a "vector" may be any agent capable of delivering or maintaining nucleic acid in a host cell, and includes viral vectors, plasmids, naked nucleic acids, nucleic acids complexed with polypeptide or other molecules and nucleic acids immobilised onto solid phase particles. Such vectors are described in detail below. It will be understood that the present invention, in its broadest form, is not limited to any specific vector for delivery of the 5T4-encoding nucleic acid.

A "nucleic acid", as referred to herein, may be DNA or RNA, naturally-occurring or synthetic, or any combination thereof. Nucleic acids according to the invention are limited only in that they serve the function of encoding 5T4 antigen in such a way that it may be translated by the machinery of the cells of a host organism. Thus, natural nucleic acids may be modified, for example to increase the stability thereof. DNA and/or RNA, but especially RNA, may be modified in order to improve nuclease resistance of the members. For example, known modifications for ribonucleotides include 2'-O-methyl, 2'-fluoro, 2'-NH$_2$, and 2'-O-allyl. The modified nucleic acids according to the invention may comprise chemical modifications which have been made in order to increase the in vivo stability of the nucleic acid, enhance or mediate the delivery thereof, or reduce the clearance rate from the body. Examples of such modifications include chemical substitutions at the ribose and/or phosphate and/or base positions of a given RNA sequence. See, for example, WO 92/03568; U.S. Pat. No. 5,118,672; Hobbs et al., (1973) Biochemistry 12:5138; Guschlbauer et al., (1977) Nucleic Acids Res. 4:1933; Schibaharu et al., (1987) Nucleic Acids Res. 15:4403; Pieken et al., (1991) Science 253:314, each of which is specifically incorporated herein by reference.

5T4 antigen is "expressed" in accordance with the present invention by being produced in the cells of a host organism as a result of translation, and optionally transcription, of the nucleic acid encoding 5T4. Thus, 5T4 is produced in situ in the cell. Since 5T4 is a transmembrane protein, the extracellular portion thereof is displayed on the surface of the cell in which it is produced. If necessary, therefore, the term "expression" includes the provision of the necessary signals to ensure correct processing of 5T4 such that it is displayed on the cell surface and can interact with the host immune system.

As used herein, the term "polypeptide" refers to a polymer in which the monomers are amino acids and are joined together through peptide or disulphide bonds. "Polypeptide" refers to a full-length naturally-occurring amino acid chain or a fragment thereof, such as a selected region of the polypeptide that is of interest in a binding interaction, or a synthetic amino acid chain, or a combination thereof. "Fragment thereof" thus refers to an amino acid sequence that is a portion of a full-length polypeptide, between about 8 and about 500 amino acids in length, preferably about 8 to about 300, more preferably about 8 to about 200 amino acids, and even more preferably about 10 to about 50 or 100 amino acids in length. Additionally, amino acids other than naturally-occurring amino acids, for example β-alanine, phenyl glycine and homoarginine, may be included. Commonly-encountered amino acids which are not gene-encoded may also be used in the present invention.

5T4 antigen is the polypeptide known as 5T4 and characterised, for example, in WO89/07947. In a preferred aspect, 5T4 is human 5T4 as characterised by Myers et al ibid., the sequence of which appears in GenBank at accession no. Z29083 and is set out herein as SEQ. ID. No. 1. The invention however comprises species and allelic variations of 5T4, including canine 5T4 set forth herein at SEQ. ID. No. 3 and mouse 5T4 set forth herein at SEQ. ID. No. 2 (GenBank Accession no. AJ012160), as well as fragments, preferably distinct epitopes, and variants thereof comprising amino acid insertions, deletions or substitutions which retain the antigenicity of 5T4. Such fragments and variants are described in greater detail below.

In a second aspect, the present invention relates to a modified 5T4 antigen. A "modified" antigen, as used herein, is a 5T4 polypeptide which has been truncated, extended or otherwise mutated such that it differs from naturally-occurring 5T4. It has been found that peptide fragments derived from 5T4 are able to function as 5T4-specific antigenic determinants. Such peptides are able to bind HLA molecules and to induce CTL responses against wild-type 5T4 in subjects, often more effectively that full-length 5T4. Moreover, 5T4 peptides may be mutated, by amino acid insertion, deletion or substitution; mutated peptides advantageously bind even more effectively to HLA and elicit an even more potent CTL response in subjects. Peptides may be any length, but are advantageously between 5 and 25 amino acids, preferably between 6 and 15 amino acids, and advantageously about 9 amino acids in length.

Modified peptides are advantageously HLA CTL epitopes of 5T4. Modification of such epitopes may be performed based on predictions for more efficient CTL induction derived using the program "Peptide Binding Predictions" devised by K. Parker (NIH) which may be found on the world wide web at bimas.dcrt.nih.gov/cgi-bin/molbio/ken parker comboform (see also Parker, K. C. et al. 1994 J.Immunol. 152:163).

In a preferred aspect, a "modified" 5T4 peptide includes peptides which have been bound or otherwise associated to transporter peptides or adjuvants, in order to increase their ability to elicit an immune response. For example, peptides may be fused to TAP independent transporter peptides for efficient transport to HLA and interaction with HLA molecules to enhance CTL epitopes (for review see Yewdell et al., 1998 J Immunother 21:127-31; Fu et al., (1998) J Virol 72:1469-81).

In a third aspect, the present invention provides a method for eliciting an immune response in a subject, comprising the steps of immunising the subject with a nucleic acid encoding 5T4 antigen, and expressing the 5T4 antigen in the subject.

An immune response is elicited, as stated, by immunisation with 5T4-expressing nucleic acid. Immunisation may be elicited through the administration of a "priming" agent comprising an antigen followed by a secondary or "boosting" agent comprising additional antigen which is administered to the immune system after it has been efficiently primed with the priming agent.

The vector employed for immunisation may be any vector, viral or non-viral. The 5T4 antigen used, whether full length 5T4 or peptides thereof, may be modified and may be homologous (i.e. derived from the same species as the subject) or heterologous in origin.

Preferably, the immune response elicited is a CTL response which involved the activation of cytotoxic T-lymphocytes which are 5T4 specific.

Advantageously, the response is an anti-tumour immunotherapeutic response which is effective to inhibit, arrest or reverse the development of a tumour in a subject.

In a fourth aspect, the present invention provides the use of a 5T4 antigen in the preparation of a composition for the immunotherapy of a tumour in a subject.

Advantageously, immunisation with a 5T4 antigen is capable of breaking immune tolerance to 5T4 in a subject.

According to a fifth aspect, the present invention provides a vaccine composition comprising 5T4 antigen. The vaccine composition may comprise a homologous 5T4 antigen, a heterologous 5T4 antigen or a mutant 5T4 antigen.

5T4 antigen-containing vaccines are useful for immunisation against, or therapy of, tumours, in a manner analogous to the use of 5T4-encoding nucleic acids for the same purposes.

Advantageously, the vaccine composition comprises one or more adjuvants.

In a sixth aspect, the invention comprises an expression vector encoding a 5T4 antigen, which vector is useful for the expression of 5T4 and the production of 5T4 antigen suitable for use in a vaccine composition. The vector may be a prokaryotic or eukaryotic vector, and is advantageously a vector capable of expressing 5T4 in mammalian cells.

The 5T4 antigen may be from any source, and may be a modified 5T4 antigen, for example as set forth herein.

In a seventh aspect, the present invention provides the use of a 5T4 antigen in the preparation of a composition for immunising a subject. Immunisation using a 5T4 comprises administering to the subject an immunologically effective amount of the vaccine composition according to the fifth aspect of the invention.

In an eighth aspect, the present invention provides the use of a 5T4 antigen in the preparation of a composition for the sterilisation of a subject. The administration of 5T4 antigen may be effective in causing sterilisation of subjects. Preferably, the subject is a female subject.

The invention further relates to the use of 5T4 targeting molecules, such as anti-5T4 antibodies, for example anti-5T4 scFvs. These antibodies may be used to (i) to target natural or exogenous 5T4 in situ and/or (ii) deliver immune enhancer molecules, such as B7.1, to natural or exogenous 5T4 in situ (Carroll et al. (1998) J Natl Cancer Inst 90(24):1881-7). This potentiates the immunogenicity of 5T4 in the subject. The present invention also relates to the sequential use of a vector encoding a 5T4 antigen and anti-5T4 antibodies, for example an anti-5T4 scFvs. The anti-5T4 scFvs antibodies may be administered as naked DNA encoding the antibodies (for example, in a plasmid comprising the encoding DNA together with a short promoter region to control its production), in an expression vector (which may be viral or non-viral) comprising the encoding sequence or in a protein form. Thus, the invention provides a vector encoding a 5T4 antigen and an agent capable of binding 5T4 which is optionally fused with an immunostimulatory molecule, for separate, such as sequential use, in the treatment of tumours.

In a further embodiment, the invention encompasses a combination therapy including enzyme/prodrug therapy and immunotherapy with 5T4. For example, the enzyme/prodrug therapy may comprise intratumoural or systemic delivery of P450, delivered optionally using an retroviral or lentiviral vector, and cyclophosphamide (CPA) followed by systemic immunotherapeutic induction with 5T4.

Thus, the invention further relates to a vector encoding 5T4 antigen a prodrug/enzyme combination, for separate, simultaneous separate or combined use in the treatment of tumours.

In a further embodiment, 5T4 or 5T4 peptides may be fused to hepatitis B core antigen to enhance T helper and antibody responses (Schodel et al., 1996 Intervirology 39:104-10).

In accordance with a ninth aspect of the invention, therefore, there is provided a recombinant poxvirus vector from which at least one immune evasion gene has been deleted, which comprises a nucleic acid sequence encoding a tumour-associated antigen (TAA).

TAAs are weakly immunogenic, being recognised as "self" by the immune system and thus tolerated to a large extent. Although the use of poxvirus vectors is able to cause the antigens to be presented such that this tolerance may be overcome at least in part, the immunogenic effect observed with most poxvirus vectors is limited. It is thought that the deletion of immune evasion genes, naturally present in poxviruses, may have a beneficial effect in vaccination with TAAs. Poxvirus vectors having deleted immune evasion genes may be capable of breaking immune tolerance to encoded self antigens, including TAAs, thus enabling a host to raise an immune response to a poorly immunogenic or other self antigen.

In a tenth aspect, the present invention provides a method for eliciting an immune response in a mammal, comprising administering to the mammal a recombinant poxvirus vector according to the ninth aspect of the invention, thereby eliciting an immune response to the TAA in the mammal.

Antigens such as TAAs are known to rely on the generation of a CTL response in order to provide a protective or therapeutic effect in a subject, which is dependent on processing of antigen via the MHCI pathway. Long-term antigen expression is thought to lead to increased longevity of high level CTL. In an eleventh aspect of the invention, there is provided a poxvirus having a reduced lytic activity for the enhancement of a CTL response to an antigen in a subject.

In a twelfth aspect, the present invention provides the use of a recombinant poxvirus vector according to the ninth or eleventh aspect of the invention, to elicit an immune response in a mammal against a TAA.

In a thirteenth aspect, the invention provides a 5T4 antigen for use as a tumour-associated target in immunotherapy.

In a fourthteenth aspect, the invention provides the use of a recombinant poxvirus vector from which at least one immune evasion gene has been deleted or mutated, which comprises a nucleic acid sequence encoding a weak immunogen, to break immune tolerance in a mammal against the weak immunogen and elicit an immune response thereto.

Other aspects of the present invention are presented in the accompanying claims and in the following description and discussion. These aspects are presented under separate section headings. However, it is to be understood that the teachings under each section heading are not necessarily limited to that particular section heading.

DETAILED DESCRIPTION OF THE INVENTION

Vectors for Delivery or Expression of 5T4 Antigen

5T4 polypeptides in accordance with the present invention can be delivered by viral or non-viral techniques.

Non-viral delivery systems include but are not limited to DNA transfection methods. Here, transfection includes a process using a non-viral vector to deliver a 5T4 gene to a target mammalian cell.

Typical transfection methods include electroporation, nucleic acid biolistics, lipid-mediated transfection, compacted nucleic acid-mediated transfection, liposomes, immunoliposomes, lipofectin, cationic agent-mediated, cationic facial amphiphiles (CFAs) (Nature Biotechnology 1996 14; 556), multivalent cations such as spermine, cationic lipids or polylysine, 1,2,-bis(oleoyloxy)-3-(trimethylammonio)propane (DOTAP)-cholesterol complexes (Wolff and Trubetskoy 1998 Nature Biotechnology 16: 421) and combinations thereof.

Viral delivery systems include but are not limited to adenovirus vectors, adeno-associated viral (AAV) vectors, herpes viral vectors, retroviral vectors, lentiviral vectors or baculoviral vectors, venezuelan equine encephalitis virus (VEE), poxviruses such as: canarypox virus (Taylor et at 1995 Vaccine 13:539-549), entomopox virus (Li Y et al 1998 XIIth International Poxvirus Symposium p 144. Abstract), penguine pox (Standard et al. J Gen Virol. 1998 79:1637-46) alphavirus, and alphavirus based DNA vectors.

Examples of retroviruses include but are not limited to: murine leukaemia virus (MLV), human immunodeficiency virus (HIV), equine infectious anaemia virus (EIAV), mouse mammary tumour virus (MMTV), Rous sarcoma virus (RSV), Fujinami sarcoma virus (FuSV), Moloney murine leukaemia virus (Mo-MLV), FBR murine osteosarcoma virus (FBR MSV), Moloney murine sarcoma virus (Mo-MSV), Abelson murine leukaemia virus (A-MLV), Avian myelocytomatosis virus-29 (MC29), and Avian erythroblastosis virus (AEV).

A detailed list of retroviruses may be found in Coffin et al ("Retroviruses" 1997 Cold Spring Harbour Laboratory Press Eds: J M Coffin, S M Hughes, H E Varmus pp 758-763).

Lentiviruses can be divided into primate and non-primate groups. Examples of primate lentiviruses include but are not limited to: the human immunodeficiency virus (HIV), the causative agent of human auto-immunodeficiency syndrome (AIDS), and the simian immunodeficiency virus (SIV). The non-primate lentiviral group includes the prototype "slow virus" visna/maedi virus (VMV), as well as the related caprine arthritis-encephalitis virus (CAEV), equine infectious anaemia virus (EIAV) and the more recently described feline immunodeficiency virus (FIV) and bovine immunodeficiency virus (BIV).

A distinction between the lentivirus family and other types of retroviruses is that lentiviruses have the capability to infect both dividing and non-dividing cells (Lewis et al 1992 EMBO. J 11: 3053-3058; Lewis and Emerman 1994 J. Virol. 68: 510-516). In contrast, other retroviruses—such as MLV—are unable to infect non-dividing cells such as those that make up, for example, muscle, brain, lung and liver tissue.

The vector of the present invention may be configured as a split-intron vector. A split intron vector is described in PCT patent applications WO 99/15.683 and WO 99/15684.

If the features of adenoviruses are combined with the genetic stability of retroviruses/lentiviruses then essentially the adenovirus can be used to transduce target cells to become transient retroviral producer cells that could stably infect neighbouring cells. Such retroviral producer cells engineered to express 5T4 antigen can be implanted in organisms such as animals or humans for use in the treatment of angiogenesis and/or cancer.

Poxvirus Vectors

Poxvirus vectors are preferred for use in the present invention. Pox viruses are engineered for recombinant gene expression and for the use as recombinant live vaccines. This entails the use of recombinant techniques to introduce nucleic acids encoding foreign antigens into the genome of the pox virus. If the nucleic acid is integrated at a site in the viral DNA which is non-essential for the life cycle of the virus, it is possible for the newly produced recombinant pox virus to be infectious, that is to say to infect foreign cells and thus to express the integrated DNA sequence. The recombinant pox virus prepared in this way can be used as live vaccines for the prophylaxis and/or treatment of pathologic and infectious disease.

Expression of 5T4 in recombinant pox viruses, such as vaccinia viruses, requires the ligation of vaccinia promoters to the nucleic acid encoding 5T4. Plasmid vectors (also called insertion vectors), have been constructed to insert nucleic acids into vaccinia virus through homologous recombination between the viral sequences flanking the nucleic acid in a donor plasmid and homologous sequence present in the parental virus (Mackett et al 1982 PNAS 79: 7415-7419). One type of insertion vector is composed of (a) a vaccinia virus promoter including the transcriptional initiation site; (b) several unique restriction endonuclease cloning sites located downstream from the transcriptional start site for insertion of nucleic acid; (c) nonessential vaccinia virus sequences (such as the Thymidine Kinase (TK) gene) flanking the promoter and cloning sites which direct insertion of the nucleic acid into the homologous nonessential region of the virus genome; and (d) a bacterial origin of replication and antibiotic resistance marker for replication and selection in E. Coli. Examples of such vectors are described by Mackett (Mackett et al 1984, J. Virol. 49: 857-864).

The isolated plasmid containing the nucleic acid to be inserted is transfected into a cell culture, e.g., chick embryo fibroblasts, along with the parental virus, e.g., poxvirus. Recombination between homologous pox DNA in the plasmid and the viral genome respectively results in a recombinant poxvirus modified by the presence of the promoter-gene construct in its genome, at a site which does not affect virus viability.

As noted above, the nucleic acid is inserted into a region (insertion region) in the virus which does not affect virus viability of the resultant recombinant virus. Such regions can be readily identified in a virus by, for example, randomly testing segments of virus DNA for regions that allow recombinant formation without seriously affecting virus viability of the recombinant. One region that can readily be used and is present in many viruses is the thymidine kinase (TK) gene. For example, the TK gene has been found in all pox virus genomes examined [leporipoxvirus: Upton, et at J. Virology 60:920 (1986) (shope fibroma virus); capripoxvirus: Gershon, et at J. Gen. Virol. 70:525 (1989) (Kenya sheep-1); orthopoxvirus: Weir, et al J. Virol 46:530 (1983) (vaccinia); Esposito, et at Virology 135:561 (1984) (monkeypox and variola virus); Hruby, et al PNAS, 80:3411 (1983) (vaccinia); Kilpatrick, et al Virology 143:399 (1985) (Yaba monkey tumour virus); avipoxvirus: Binns, et at J. Gen. Virol 69:1275 (1988) (fowlpox); Boyle, et al Virology 156:355 (1987) (fowlpox); Schnitzlein, et al J. Virological Method, 20:341 (1988) (fowlpox, quailpox); entomopox (Lytvyn, et al J. Gen. Virol 73:3235-3240 (1992)].

In vaccinia, in addition to the TK region, other insertion regions include, for example, HindIII M.

In fowlpox, in addition to the TK region, other insertion regions include, for example, BamHI J [Jenkins, et al AIDS Research and Human Retroviruses 7:991-998 (1991)] the EcoRI-HindIII fragment, BamHI fragment, EcoRV-HindIII fragment, BamHI fragment and the HindIII fragment set forth in EPO Application No. 0 308 220 A1. [Calvert, et al J. of Virol 67:3069-3076 (1993); Taylor, et al Vaccine 6:497-503 (1988); Spehner, et al (1990) and Boursnell, et al J. of Gen. Virol 71:621-628 (1990)].

In swinepox preferred insertion sites include the thymidine kinase gene region.

A promoter can readily be selected depending on the host and the target cell type. For example in poxviruses, pox viral promoters should be used, such as the vaccinia 7.5K, or 40K or fowlpox C1. Artificial constructs containing appropriate pox sequences can also be used. Enhancer elements can also be used in combination to increase the level of expression. Furthermore, the use of inducible promoters, which are also well known in the art, are preferred in some embodiments.

Foreign gene expression can be detected by enzymatic or immunological assays (for example, immuno-precipitation, radioimmunoassay, or immnunoblotting). Naturally occurring membrane glycoproteins produced from recombinant vaccinia infected cells are glycosylated and may be transported to the cell surface. High expressing levels can be obtained by using strong promoters.

Other requirements for viral vectors for use in vaccines include good immunogenicity and safety. MVA is a replication-impaired vaccinia strain with a good safety record. In most cell types and normal human tissue, MVA does not replicate. Replication of MVA is observed in a few transformed cell types such as BHK21 cells. Carroll et al (1997) have shown that the recombinant MVA is equally as good as conventional recombinant vaccinia vectors at generating a protective CD8+T cell response and is an efficacious alternative to the more commonly used replication competent vaccinia virus. The vaccinia virus strains derived from MVA, or independently developed strains having the features of MVA which make MVA particularly suitable for use in a vaccine, are also suitable for use in the present invention.

Preferably, the vector is a vaccinia virus vector such as MVA or NYVAC. Most preferred is the vaccinia strain modified virus ankara (MVA) or a strain derived therefrom. Alternatives to vaccinia vectors include avipox vectors such as fowlpox or canarypox known as ALVAC and strains derived therefrom which can infect and express recombinant proteins in human cells but are unable to replicate.

In one aspect of the present invention at least one immune evasion gene is deleted from the poxvirus vector.

Viruses, especially large viruses such a poxviruses which have an extensive coding capacity and can thus encode a variety of genes, have developed a number of techniques for evading the immune system of their hosts. For example, they are able to evade non-specific defences such as complement, interferons and the inflammatory response, as well as to interfere with or block the function of cytokines. A number of these immune evasion polypeptides have been deleted from MVA, with the exception of the interferon resistance protein in the left terminal region.

Poxviruses in general, being large DNA viruses which establish acute, rather than latent, infections. They encode so many antigenic proteins that antigenic variation is difficult, thus relying on active immune evasion to protect themselves from the mammalian immune system. They possess a number of genes which encode polypeptides which are responsible for interfering with a number of aspects of the immune system: they disrupt interferon action, interfere with complement, cytokine activity, inflammatory responses and CTL recognition (for a review, Smith et al., (1997) Immunol Rev 159:137-154). Removal of these proteins is beneficial in promoting the ability of weak immunogens encoded on a poxvirus vector to elicit an immune response in a subject.

An immune evasion gene or polypeptide is a gene, or its product, which assists the virus in evading the mammalian immune system. Preferably, the gene or gene product interferes with the working of the immune system, at least one level. This may be achieved in a number of ways, such as by interfering in signalling pathways by providing competitors for signalling molecules, by providing soluble cytokine receptor mimics and the like.

Immune evasion genes include, but are not limited to, the following:

Interferon evasion genes. Vaccinia possesses at least three genes which interfere with IFN action. The E3L gene expresses a 25 Kd polypeptide which competes with P1 protein kinase for binding to dsRNA, an event which leads to activation of P1, phosphorylation of eIF2α and resultant failure of translation initiation complex assembly. This pathway is ordinarily responsive to IFN activation, but is impeded by E3L expression thus allowing translation initiation to proceed unimpeded.

The K3L gene expresses a 10.5 Kd polypeptide which also interferes with P1 activity, since it is effectively an eIF2α mimic and acts as a competitor for P1 protein kinase. Its mode of action is thus similar to E3L.

The A18R gene is predicted to encode a helicase, which appears to interfere with the 2',5'-oligoadenylate pathway, which is in turn IFN responsive. 2',5'-A activates RNAse L, which acts to prevent viral translation. Expression of A18R appears to reduce 2',5'-A levels in infected cells.

Complement. The product of the B5R gene of vaccinia is known to be highly related to factor H, a regulator of the alternative complement pathway. This pathway may be activated by antigen alone, unlike the classical pathway. The B5R gene product thus may interfere with the alternative complement pathway.

The C21L gene is in turn related to C4b-binding protein in humans, and interacts with cells bearing C4b on the surface to prevent binding to the CR1 complement receptor.

Soluble Cytokine Receptors. The product of the vaccinia WR B15R gene (B16R in Copenhagen strain vaccinia) is related to IL1-R, the receptor for IL-1β.

The WR gene ORF SalF19R, A53R in Copenhagen strain vaccinia, encodes a TNF receptor. However, in wild-type virus both of these genes are believed to be inactive due to fragmentation of the ORFs.

The B8R gene is believed to encode a soluble IFN-γ receptor, providing the virus with yet another IFN evasion mechanism.

Inflammation. A number of genes are believed to be involved in the prevention of inflammatory responses to viral infection. These include A44L, K2L, B13R and B22R.

In one aspect of the present invention, the majority of the immune evasion genes are deleted from the recombinant poxvirus vector. Preferably, all the immune evasion genes are deleted. Thus, in one aspect of the present invention, the recombinant poxvirus vector is a recombinant MVA vector in which the K3L interferon resistance protein gene has been disrupted or deleted.

Preferred are poxviruses which are non-hazardous to the intended subject. Thus, for example, for use in humans, poxviruses which are either host-range restricted, such as avipox viruses, or otherwise attenuated, such as attenuated strains of vaccinia (including NYVAC and MVA) are preferred. Most preferred are attenuated vaccinia virus strains, although non-vaccinia strains are usefully employed in subjects with pre-existing smallpox immunity.

A construct which contains at least one nucleic acid which codes for 5T4 flanked by MVA DNA sequences adjacent to a naturally occurring deletion, e.g. deletion II, within the MVA genome, is introduced into cells infected with MVA, to allow homologous recombination.

Once the construct has been introduced into the eukaryotic cell and the 5T4 DNA has recombined with the viral DNA, the desired recombinant vaccinia virus, can be isolated, preferably with the aid of a marker (Nakano et al Proc. Natl. Acad. Sci. USA 79, 1593-1596 [1982], Franke et al Mol. Cell. Biol. 1918-1924 [1985], Chakrabarti et al Mol. Cell. Biol. 3403-3409 [1985], Fathi et al Virology 97-105 [1986]).

The construct to be inserted can be linear or circular. A circular DNA is preferred, especially a plasmid. The construct contains sequences flanking the left and the right side of a naturally occurring deletion, e.g. deletion II, within the MVA genome (Altenburger, W., Suter, C. P. and Altenburger J. (1989) Arch. Virol. 105, 15-27). The foreign DNA sequence is inserted between the sequences flanking the naturally occurring deletion.

For the expression of at least one nucleic acid, it is necessary for regulatory sequences, which are required for the transcription of the nucleic acid to be present upstream of the nucleic acid. Such regulatory sequences are known to those skilled in the art, and includes for example those of the vaccinia 11 kDa gene as are described in EP-A-198,328, and those of the 7.5 kDa gene (EP-A-110,385).

The construct can be introduced into the MVA infected cells by transfection, for example by means of calcium phosphate precipitation (Graham et al Virol. 52, 456-467 [1973; Wigler et al Cell 777-785 [1979] by means of electroporation (Neumann et al EMBO J. 1, 841-845 [1982]), by microinjection (Graessmann et al Meth. Enzymology 101, 482-492

(1983)), by means of liposomes (Straubinger et al Methods in Enzymology 101, 512-527 (1983)), by means of spheroplasts (Schaffner, Proc. Natl. Acad. Sci. USA 77, 2163-2167 (1980)) or by other methods known to those skilled in the art. Transfection by means of liposomes is preferred.

The recombinant priming and boosting vectors of the present invention can have a tropism for a specific cell type in the mammal. By way of example, the recombinant vectors of the present invention can be engineered to infect professional APCs such as dendritic cells and macrophages. Dendritic cells are known to be orchestrators of a successful immune response especially that of a cell mediated response. It has been shown that ex vivo treatment of dendritic cells with antigen or viral vectors containing such a target antigen, will induce efficacious immune responses when infused into syngeneic animals or humans (see Nestle F O, et al. Vaccination of melanoma patients with peptide- or tumor lysate-pulsed dendritic cells, Nat Med. March 1998;4(3):328-32 and Kim C J, et al. Dendritic cells infected with poxviruses encoding MART-1/Melan A sensitize T lymphocytes in vitro. J Immunother. July 1997;20(4):276-86. The recombinant vectors can also infect tumour cells. Alternatively, the recombinant vectors are able to infect any cell in the mammal.

Other examples of vectors include ex vivo delivery systems, which include but are not limited to DNA transfection methods such as electroporation, DNA biolistics, lipid-mediated transfection and compacted DNA-mediated transfection.

The vector may be a plasmid DNA vector. As used herein, "plasmid" refers to discrete elements that are used to introduce heterologous DNA into cells for either expression or replication thereof. Selection and use of such vehicles are well within the skill of the artisan. Many plasmids are available, and selection of appropriate plasmid will depend on the intended use of the plasmid, i.e. whether it is to be used for DNA amplification or for DNA expression, the size of the DNA to be inserted into the plasmid, and the host cell to be transformed with the plasmid. Each plasmid contains various components depending on its function (amplification of DNA or expression of DNA) and the host cell for which it is compatible. The plasmid components generally include, but are not limited to, one or more of the following: an origin of replication, one or more marker genes, an enhancer element, a promoter, a transcription termination sequence and a signal sequence.

Both expression and cloning plasmids generally contain nucleic acid sequence that enable the plasmid to replicate in one or more selected host cells. Typically in cloning plasmids, this sequence is one that enables the plasmid to replicate independently of the host chromosomal DNA, and includes origins of replication or autonomously replicating sequences. Such sequences are well known for a variety of bacteria, yeast and viruses. The origin of replication from the plasmid pBR322 is suitable for most Gram-negative bacteria, the 2 m plasmid origin is suitable for yeast, and various viral origins (e.g. SV 40, polyoma, adenovirus) are useful for cloning plasmids in mammalian cells. Generally, the origin of replication component is not needed for mammalian expression plasmids unless these are used in mammalian cells competent for high level DNA replication, such as COS cells.

Most expression plasmids are shuttle plasmids, i.e. they are capable of replication in at least one class of organisms but can be transfected into another class of organisms for expression. For example, a plasmid is cloned in E. Coli and then the same plasmid is transfected into yeast or mammalian cells even though it is not capable of replicating independently of the host cell chromosome.

Advantageously, an expression and cloning plasmid may contain a selection gene also referred to as selectable marker. This gene encodes a protein necessary for the survival or growth of transformed host cells grown in a selective culture medium. Host cells not transformed with the plasmid containing the selection gene will not survive in the culture medium. Typical selection genes encode proteins that confer resistance to antibiotics and other toxins, e.g. ampicillin, neomycin, methotrexate or tetracycline, complement auxotrophic deficiencies, or supply critical nutrients not available from complex media.

As to a selective gene marker appropriate for yeast, any marker gene can be used which facilitates the selection for transformants due to the phenotypic expression of the marker gene. Suitable markers for yeast are, for example, those conferring resistance to antibiotics G418, hygromycin or bleomycin, or provide for prototrophy in an auxotrophic yeast mutant, for example the URA3, LEU2, LYS2, TRP1, or HIS3 gene.

Since the replication of plasmids is conveniently done in E. Coli, an E. Coli genetic marker and an E. Coli origin of replication are advantageously included. These can be obtained from E. Coli plasmids, such as pBR322, Bluescript© plasmid or a pUC plasmid, e.g. pUC18 or pUC19, which contain both E. Coli replication origin and E. Coli genetic marker conferring resistance to antibiotics, such as ampicillin.

Suitable selectable markers for mammalian cells are those that enable the identification of cells which have taken up 5T4 nucleic acid, such as dihydrofolate reductase (DHFR, methotrexate resistance), thymidine kinase, or genes conferring resistance to G418 or hygromycin. The mammalian cell transformants are placed under selection pressure which only those transformants which have taken up and are expressing the marker are uniquely adapted to survive. In the case of a DHFR or glutamine synthase (GS) marker, selection pressure can be imposed by culturing the transformants under conditions in which the pressure is progressively increased, thereby leading to amplification (at its chromosomal integration site) of both the selection gene and the linked DNA that encodes 5T4. Amplification is the process by which genes in greater demand for the production of a protein critical for growth, together with closely associated genes which may encode a desired protein, are reiterated in tandem within the chromosomes of recombinant cells. Increased quantities of desired protein are usually synthesised from thus amplified DNA.

Expression and cloning plasmids usually contain a promoter that is recognised by the host organism and is operably linked to 5T4 nucleic acid. Such a promoter may be inducible or constitutive. The promoters are operably linked to DNA encoding 5T4 by removing the promoter from the source DNA by restriction enzyme digestion and inserting the isolated promoter sequence into the plasmid. Both the native 5T4 promoter sequence and many heterologous promoters may be used to direct amplification and/or expression of 5T4 DNA. The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences.

Promoters suitable for use with prokaryotic hosts include, for example, the β-lactamase and lactose promoter systems, alkaline phosphatase, the tryptophan (trp) promoter system and hybrid promoters such as the tac promoter. Their nucleotide sequences have been published, thereby enabling the skilled worker operably to ligate them to DNA encoding 5T4, using linkers or adaptors to supply any required restriction sites. Promoters for use in bacterial systems will also generally contain a Shine-Delgarno sequence operably-linked to the DNA encoding 5T4.

Preferred expression plasmids are bacterial expression plasmids which comprise a promoter of a bacteriophage such as phagex or T7 which is capable of functioning in the bacteria. In one of the most widely used expression systems, the nucleic acid encoding the fusion protein may be transcribed from the plasmid by T7 RNA polymerase (Studier et al, Methods in Enzymol. 185; 60-89, 1990). In the E. Coli BL21 (DE3) host strain, used in conjunction with pET plasmids, the T7 RNA polymerase is produced from the λ-lysogen DE3 in the host bacterium, and its expression is under the control of the IPTG inducible lac UV5 promoter. This system has been employed successfully for over-production of many proteins. Alternatively the polymerase gene may be introduced on a lambda phage by infection with an int-phage such as the CE6 phage which is commercially available (Novagen, Madison, USA). other plasmids include plasmids containing the lambda PL promoter such as PLEX (Invitrogen, NL), plasmids containing the trc promoters such as pTrcHisXpress™ (Invitrogen) or pTrc99 (Pharmacia Biotech, SE), or plasmids containing the tac promoter such as pKK223-3 (Pharmacia Biotech) or PMAL (new England Biolabs, MA, USA).

Moreover, the 5T4 gene according to the invention preferably includes a secretion sequence in order to facilitate secretion of the polypeptide from bacterial hosts, such that it will be produced as a soluble native peptide rather than in an inclusion body.

The peptide may be recovered from the bacterial periplasmic space, or the culture medium, as appropriate.

Suitable promoting sequences for use with yeast hosts may be regulated or constitutive and are preferably derived from a highly expressed yeast gene, especially a *Saccharomyces cerevisiae* gene. Thus, the promoter of the TRP1 gene, the ADHI or ADHII gene, the acid phosphatase (PH05) gene, a promoter of the yeast mating pheromone genes coding for the a- or α-factor or a promoter derived from a gene encoding a glycolytic enzyme such as the promoter of the enolase, glyceraldehyde-3-phosphate dehydrogenase (GAP), 3-phospho glycerate kinase (PGK), hexokinase, pyruvate decarboxylase, phosphofructokinase, glucose-6-phosphate isomerase, 3-phosphoglycerate mutase, pyruvate kinase, triose phosphate isomerase, phosphoglucose isomerase or glucokinase genes, the *S. cerevisiae* GAL 4 gene, the *S. pombe* nmt 1 gene or a promoter from the TATA binding protein (TBP) gene can be used. Furthermore, it is possible to use hybrid promoters comprising upstream activation sequences (UAS) of one yeast gene and downstream promoter elements including a functional TATA box of another yeast gene, for example a hybrid promoter including the UAS(s) of the yeast PH05 gene and downstream promoter elements including a functional TATA box of the yeast GAP gene (PH05-GAP hybrid promoter). A suitable constitutive PHO5 promoter is e.g. a shortened acid phosphatase PH05 promoter devoid of the upstream regulatory elements (UAS) such as the PH05 (−173) promoter element starting at nucleotide −173 and ending at nucleotide −9 of the PH05 gene.

5T4 gene transcription from plasmids in mammalian hosts may be controlled by promoters derived from the genomes of viruses such as polyoma virus, adenovirus, fowlpox virus, bovine papilloma virus, avian sarcoma virus, cytomegalovirus (CMV), a retrovirus and Simian Virus 40 (SV40), from heterologous mammalian promoters such as the actin promoter or a very strong promoter, e.g. a ribosomal protein promoter, and from the promoter normally associated with 5T4 sequence, provided such promoters are compatible with the host cell systems.

Transcription of a DNA encoding 5T4 by higher eukaryotes may be increased by inserting an enhancer sequence into the plasmid. Enhancers are relatively orientation and position independent. Many enhancer sequences are known from mammalian genes (e.g. elastase and globin). However, typically one will employ an enhancer from a eukaryotic cell virus. Examples include the SV40 enhancer on the late side of the replication origin (bp 100-270) and the CMV early promoter enhancer. The enhancer may be spliced into the plasmid at a position 5' or 3' to 5T4 DNA, but is preferably located at a site 5' from the promoter.

Advantageously, a eukaryotic expression plasmid encoding 5T4 may comprise a locus control region (LCR). LCRs are capable of directing high-level integration site independent expression of transgenes integrated into host cell chromatin, which is of importance especially where the 5T4 gene is to be expressed in the context of a permanently-transfected eukaryotic cell line in which chromosomal integration of the plasmid has occurred, in plasmids designed for gene therapy applications or in transgenic animals.

Eukaryotic expression plasmids will also contain sequences necessary for the termination of transcription and for stabilising the mRNA. Such sequences are commonly available from the 5' and 3' untranslated regions of eukaryotic or viral DNAs or cDNAs. These regions contain nucleotide segments transcribed as polyadenylated fragments in the untranslated portion of the mRNA encoding 5T4.

An expression plasmid includes any plasmid capable of expressing 5T4 nucleic acids that are operatively linked with regulatory sequences, such as promoter regions, that are capable of expression of such DNAs. Thus, an expression plasmid refers to a recombinant DNA or RNA construct, such as a plasmid, a phage, recombinant virus or other plasmid, that upon introduction into an appropriate host cell, results in expression of the cloned DNA. Appropriate expression plasmids are well known to those with ordinary skill in the art and include those that are replicable in eukaryotic and/or prokaryotic cells and those that remain episomal or those which integrate into the host cell genome. For example, DNAs encoding 5T4 may be inserted into a plasmid suitable for expression of cDNAs in mammalian cells, e.g. a CMV enhancer-based plasmid such as pEVRF (Matthias, et al., (1989) NAR 17, 6418).

Particularly useful for practising the present invention are expression plasmids that provide for the transient expression of DNA encoding 5T4 in mammalian cells. Transient expression usually involves the use of an expression plasmid that is able to replicate efficiently in a host cell, such that the host cell accumulates many copies of the expression plasmid, and, in turn, synthesises high levels of 5T4. For the purposes of the present invention, transient expression systems are useful e.g. for identifying 5T4 mutants, to identify potential phosphorylation sites, or to characterise functional domains of the protein.

Construction of plasmids according to the invention employs conventional ligation techniques. Isolated plasmids or DNA fragments are cleaved, tailored, and religated in the form desired to generate the plasmids required. If desired, analysis to confirm correct sequences in the constructed plasmids is performed in a known fashion. Suitable methods for constructing expression plasmids, preparing in vitro transcripts, introducing DNA into host cells, and performing analyses for assessing 5T4 expression and function are known to those skilled in the art. Gene presence, amplification and/or expression may be measured in a sample directly, for example, by conventional Southern blotting, Northern blotting to quantitate the transcription of mRNA, dot blotting (DNA or RNA analysis), or in situ hybridisation, using an appropriately labelled probe which may be based on a sequence provided herein. Those skilled in the art will readily envisage how these methods may be modified, if desired.

5T4 Antigen, Fragments and Variants

5T4 antigen, as referred to herein, includes peptides and other fragments of 5T4 which retain at least one common antigenic determinant of 5T4.

"Common antigenic determinant" means that the derivative in question at least one antigenic function of 5T4. Antigenic functions includes possession of an epitope or antigenic site that is capable of cross-reacting with antibodies raised against a naturally occurring or denatured 5T4 polypeptide or fragment thereof, or the ability to bind HLA molecules and induce a 5T4-specific immune response. Thus 5T4 as provided by the present invention includes splice variants encoded by mRNA generated by alternative splicing of a primary transcript, amino acid mutants, glycosylation variants and other covalent derivatives of 5T4 which retain the physiological and/or physical properties of 5T4. Exemplary derivatives include molecules wherein the protein of the invention is covalently modified by substitution, chemical, enzymatic, or other appropriate means with a moiety other than a naturally occurring amino acid. Such a moiety may be a detectable moiety such as an enzyme or a radioisotope. Further included are naturally occurring variants of 5T4 found with a particular species, preferably a mammal. Such a variant may be encoded by a related gene of the same gene family, by an allelic variant of a particular gene, or represent an alternative splicing variant of the 5T4 gene.

Derivatives which retain common antigenic determinants can be fragments of 5T4. Fragments of 5T4 comprise individual domains thereof, as well as smaller polypeptides derived from the domains. Preferably, smaller polypeptides derived from 5T4 according to the invention define a single epitope which is characteristic of 5T4. Fragments may in theory be almost any size, as long as they retain one characteristic of 5T4. Preferably, fragments will be between 5 and 400 amino acids in length. Longer fragments are regarded as truncations of the full-length 5T4 and generally encompassed by the term "5T4". Advantageously, fragments are relatively small peptides of the order of 5 to 25 amino acids in length. Preferred are peptides about 9 amino acids in length.

Derivatives of 5T4 also comprise mutants thereof, which may contain amino acid deletions, additions or substitutions, subject to the requirement to maintain at least one feature characteristic of 5T4. Thus, conservative amino acid substitutions may be made substantially without altering the nature of 5T4, as may truncations from the 5' or 3' ends. Deletions and substitutions may moreover be made to the fragments of 5T4 comprised by the invention. 5T4 mutants may be produced from a DNA encoding 5T4 which has been subjected to in vitro mutagenesis resulting e.g. in an addition, exchange and/or deletion of one or more amino acids. For example, substitutional, deletional or insertional variants of 5T4 can be prepared by recombinant methods and screened for immuno-crossreactivity with the native forms of 5T4.

Moreover, variant peptides can be screened for superior HLA binding capabilities using the program "Peptide Binding Predictions" devised by K. Parker at the National Institutes of Health (see Parker, K. C et al. 1994. J. Immunol. 152:163).

The fragments, mutants and other derivative of 5T4 preferably retain substantial homology with 5T4. As used herein, "homology" means that the two entities share sufficient characteristics for the skilled person to determine that they are similar in origin and function. Preferably, homology is used to refer to sequence identity. Thus, the derivatives of 5T4 preferably retain substantial sequence identity with the sequence of SEQ ID No. 2.

"Substantial homology", where homology indicates sequence identity, means more than 40% sequence identity, preferably more than 45% sequence identity and most preferably a sequence identity of 50% or more, as judged by direct sequence alignment and comparison.

Sequence homology (or identity) may moreover be determined using any suitable homology algorithm, using for example default parameters. Advantageously, the BLAST algorithm is employed, with parameters set to default values. The BLAST algorithm is described in detail on the world wide web at ncbi.nih.gov/BLAST/blast_help.html. The search parameters are defined as follows, and are advantageously set to the defined default parameters.

Advantageously, "substantial homology" when assessed by BLAST equates to sequences which match with an EXPECT value of at least about 7, preferably at least about 9 and most preferably 10 or more. The default threshold for EXPECT in BLAST searching is usually 10.

BLAST (Basic Local Alignment Search Tool) is the heuristic search algorithm employed by the programs blastp, blastn, blastx, tblastn, and tblastx; these programs ascribe significance to their findings using the statistical methods of Karlin and Altschul (see ncbi.nih.gov/BLAST/blast_help.html on the world wide web) with a few enhancements. The BLAST programs were tailored for sequence similarity searching, for example to identify homologues to a query sequence. The programs are not generally useful for motif-style searching. For a discussion of basic issues in similarity searching of sequence databases, see Alschul et al. (1994) Nature Genetics 6:119-129.

The five BLAST programs available on the world wide web at ncbi.nlm.nih.gov perform the following tasks:

blastp compares an amino acid query sequence against a protein sequence database;

blastn compares a nucleotide query sequence against a nucleotide sequence database;

blastx compares the six-frame conceptual translation products of a nucleotide query sequence (both strands) against a protein sequence database;

tblastn compares a protein query sequence against a nucleotide sequence database dynamically translated in all six reading frames (both strands).

tblastx compares the six-frame translations of a nucleotide query sequence against the six-frame translations of a nucleotide sequence database.

BLAST uses the following search parameters:

HISTOGRAM Display a histogram of scores for each search; default is yes. (See parameter H in the BLAST Manual).

DESCRIPTIONS Restricts the number of short descriptions of matching sequences reported to the number specified; default limit is 100 descriptions. (See parameter V in the manual page). See also EXPECT and CUTOFF.

ALIGNMENTS Restricts database sequences to the number specified for which high-scoring segment pairs (HSPs) are reported; the default limit is 50. If more database sequences than this happen to satisfy the statistical significance threshold for reporting (see EXPECT and CUTOFF below), only the matches ascribed the greatest statistical significance are reported. (See parameter B in the BLAST Manual).

EXPECT The statistical significance threshold for reporting matches against database sequences; the default value is 10, such that 10 matches are expected to be found merely by chance, according to the stochastic model of Karlin and Altschul (1990). If the statistical significance ascribed to a match is greater than the EXPECT threshold, the match will not be reported. Lower EXPECT thresholds are more stringent, leading to fewer chance matches being reported. Fractional values are acceptable. (See parameter E in the BLAST Manual).

CUTOFF Cutoff score for reporting high-scoring segment pairs. The default value is calculated from the EXPECT value (see above). HSPs are reported for a database sequence only if the statistical significance ascribed to them is at least as high as would be ascribed to a lone HSP having a score equal to the CUTOFF value. Higher CUTOFF values are more stringent, leading to fewer chance matches being reported. (See parameter S in the BLAST Manual). Typically, significance thresholds can be more intuitively managed using EXPECT.

MATRIX Specify an alternate scoring matrix for BLASTP, BLASTX, TBLASTN and TBLASTX. The default matrix is BLOSUM62 (Henikoff & Henikoff, 1992). The valid alternative choices include: PAM40, PAM120, PAM250 and IDENTITY. No alternate scoring matrices are available for BLASTN; specifying the MATRIX directive in BLASTN requests returns an error response.

STRAND Restrict a TBLASTN search to just the top or bottom strand of the database sequences; or restrict a BLASTN, BLASTX or TBLASTX search to just reading frames on the top or bottom strand of the query sequence.

FILTER Mask off segments of the query sequence that have low compositional complexity, as determined by the SEG program of Wootton & Federhen (1993) Computers and Chemistry 17:149-163, or segments consisting of short-periodicity internal repeats, as determined by the XNU program of Claverie & States (1993) Computers and Chemistry 17:191-201, or, for BLASTN, by the DUST program of Tatusov and Lipman (see ncbi.nlm.nih.gov on the world wide web). Filtering can eliminate statistically significant biologically uninteresting reports from the blast output (e.g., hits against common acidic-, basic- or proline-rich regions), leaving the more biologically interesting regions of the query sequence available for specific matching against database sequences.

Low complexity sequence found by a filter program is substituted using the letter "N" in nucleotide sequence (e.g., "NNNNNNNNNNNNN") and the letter "X" in protein sequences (e.g., "XXXXXXXXX").

Filtering is only applied to the query sequence (or its translation products), not to database sequences. Default filtering is DUST for BLASTN, SEG for other programs.

It is not unusual for nothing at all to be masked by SEG, XNU, or both, when applied to sequences in SWISS-PROT, so filtering should not be expected to always yield an effect. Furthermore, in some cases, sequences are masked in their entirety, indicating that the statistical significance of any matches reported against the unfiltered query sequence should be suspect.

NCBI-gi Causes NCBI gi identifiers to be shown in the output, in addition to the accession and/or locus name.

More preferably, sequence comparisons are conducted using the simple BLAST search algorithm provided at on the world wide web at ncbi.nlm.nih.gov/BLAST.

Alternatively, sequence homology may be determined by algorithms such as FastA, available at on the internet at biology.ncsa.uiuc.edu/BW30/BW.cgi. FastA is considered to be superior to BLAST for alignment of short sequences. Advantageously, the FastA algorithm is employed using default parameters.

Preferably, the protein or derivative thereof of the invention is provided in isolated form. "Isolated" means that the protein or derivative has been identified and is free of one or more components of its natural environment. Isolated 5T4 includes 5T4 in a recombinant cell culture. 5T4 present in an organism expressing a recombinant 5T4 gene, whether the 5T4 protein is "isolated" or otherwise, is included within the scope of the present invention.

In the vaccination of humans against tumours, the use of non-human TAAs is preferred. The invention accordingly provides canine 5T4. Canine 5T4 is advantageously provided for use as a vaccine component in humans, in order to elicit an immune response to human 5T4 in a human subject.

The sequence of canine 5T4 is set forth in SEQ. ID. No. 3. Sequences from other canine sources are obtainable by those skilled in the art, for example by hybridisation with a nucleic acid probe derived from SEQ. ID. No. 3.

Exemplary nucleic acids can thus be characterised as those nucleotide sequences which encode a canine 5T4 protein and hybridise to the DNA sequences set forth SEQ ID No. 3, or a selected fragment of said DNA sequence. Preferred are such sequences encoding canine 5T4 which hybridise under high-stringency conditions to the sequence of SEQ ID No. 3.

Stringency of hybridisation refers to conditions under which polynucleic acid hybrids are stable. Such conditions are evident to those of ordinary skill in the field. As known to those of skill in the art, the stability of hybrids is reflected in the melting temperature (Tm) of the hybrid which decreases approximately 1 to 1.5° C. with every 1% decrease in sequence homology. In general, the stability of a hybrid is a function of sodium ion concentration and temperature. Typically, the hybridisation reaction is performed under conditions of higher stringency, followed by washes of varying stringency.

As used herein, high stringency refers to conditions that permit hybridisation of only those nucleic acid sequences that form stable hybrids in 1 M Na+ at 65-68° C. High stringency conditions can be provided, for example, by hybridisation in an aqueous solution containing 6×SSC, 5× Denhardt's, 1% SDS (sodium dodecyl sulphate), 0.1 Na+ pyrophosphate and 0.1 mg/ml denatured salmon sperm DNA as non specific competitor. Following hybridisation, high stringency washing may be done in several steps, with a final wash (about 30 min) at the hybridisation temperature in 0.2-0.1×SSC, 0.1% SDS.

Moderate stringency refers to conditions equivalent to hybridisation in the above described solution but at about 60-62° C. In that case the final wash is performed at the hybridisation temperature in 1×SSC, 0.1% SDS.

Low stringency refers to conditions equivalent to hybridisation in the above described solution at about 50-52° C. In that case, the final wash is performed at the hybridisation temperature in 2×SSC, 0.1% SDS.

It is understood that these conditions may be adapted and duplicated using a variety of buffers, e.g. formamide-based buffers, and temperatures. Denhardt's solution and SSC are well known to those of skill in the art as are other suitable hybridisation buffers (see, e.g. Sambrook, et al., eds. (1989) Molecular Cloning: A Laboratory Manual, Cold Spring Harbor Laboratory Press, New York or Ausubel, et al., eds. (1990) Current Protocols in Molecular Biology, John Wiley & Sons, Inc.). Optimal hybridisation conditions have to be determined empirically, as the length and the GC content of the probe also play a role.

Advantageously, the invention moreover provides nucleic acid sequence which are capable of hybridising, under stringent conditions, to a fragment of SEQ. ID. No. 3. Preferably, the fragment is between 15 and 50 bases in length. Advantageously, it is about 25 bases in length.

Given the guidance provided herein, the nucleic acids of the invention are obtainable according to methods well known in the art. For example, a DNA of the invention is obtainable by chemical synthesis, using polymerase chain reaction (PCR) or by screening a genomic library or a suitable cDNA library prepared from a source believed to possess canine 5T4 and to express it at a detectable level.

Chemical methods for synthesis of a nucleic acid of interest are known in the art and include triester, phosphite, phosphoramidite and H-phosphonate methods, PCR and other autoprimer methods as well as oligonucleotide synthesis on solid supports. These methods may be used if the entire nucleic acid sequence of the nucleic acid is known, or the sequence of the nucleic acid complementary to the coding strand is available. Alternatively, if the target amino acid sequence is known, one may infer potential nucleic acid sequences using known and preferred coding residues for each amino acid residue.

An alternative means to isolate the gene encoding canine 5T4 is to use PCR technology as described e.g. in section 14 of Sambrook et al., 1989. This method requires the use of oligonucleotide probes that will hybridise to canine 5T4 nucleic acid. Strategies for selection of oligonucleotides are described below.

Libraries are screened with probes or analytical tools designed to identify the gene of interest or the protein encoded by it. For cDNA expression libraries suitable means include monoclonal or polyclonal antibodies that recognise and specifically bind to canine 5T4; oligonucleotides of about 20 to 80 bases in length that encode known or suspected canine 5T4 cDNA from the same or different species; and/or complementary or homologous cDNAs or fragments thereof that encode the same or a hybridising gene. Appropriate probes for screening genomic DNA libraries include, but are not limited to oligonucleotides, cDNAs or fragments thereof that encode the same or hybridising DNA; and/or homologous genomic DNAs or fragments thereof.

A nucleic acid encoding canine 5T4 may be isolated by screening suitable cDNA or genomic libraries under suitable hybridisation conditions with a probe, i.e. a nucleic acid disclosed herein including oligonucleotides derivable from the sequences set forth in SEQ ID NO. 3. Suitable libraries are commercially available or can be prepared e.g. from cell lines, tissue samples, and the like.

As used herein, a probe is e.g. a single-stranded DNA or RNA that has a sequence of nucleotides that includes between 10 and 50, preferably between 15 and 30 and most preferably at least about 20 contiguous bases that are the same as (or the complement of) an equivalent or greater number of contiguous bases set forth in SEQ ID No. 3. The nucleic acid sequences selected as probes should be of sufficient length and sufficiently unambiguous so that false positive results are minimised. The nucleotide sequences are usually based on conserved or highly homologous nucleotide sequences or regions of canine 5T4. The nucleic acids used as probes may be degenerate at one or more positions. The use of degenerate oligonucleotides may be of particular importance where a library is screened from a species in which preferential codon usage in that species is not known.

Preferred regions from which to construct probes include 5' and/or 3' coding sequences, sequences predicted to encode ligand binding sites, and the like. For example, either the full-length cDNA clone disclosed herein or fragments thereof can be used as probes. Preferably, nucleic acid probes of the invention are labelled with suitable label means for ready detection upon hybridisation. For example, a suitable label means is a radiolabel. The preferred method of labelling a DNA fragment is by incorporating α32P dATP with the Klenow fragment of DNA polymerase in a random priming reaction, as is well known in the art. Oligonucleotides are usually end-labelled With γ32P-labelled ATP and polynucleotide kinase. However, other methods (e.g. non-radioactive) may also be used to label the fragment or oligonucleotide, including e.g. enzyme labelling, fluorescent labelling with suitable fluorophores and biotinylation.

After screening the library, e.g. with a portion of DNA including substantially the entire canine 5T4-encoding sequence or a suitable oligonucleotide based on a portion of said DNA, positive clones are identified by detecting a hybridisation signal; the identified clones are characterised by restriction enzyme mapping and/or DNA sequence analysis, and then examined, e.g. by comparison with the sequences set forth herein, to ascertain whether they include DNA encoding a complete canine 5T4 (i.e., if they include translation initiation and termination codons). If the selected clones are incomplete, they may be used to rescreen the same or a different library to obtain overlapping clones. If the library is genomic, then the overlapping clones may include exons and introns. If the library is a cDNA library, then the overlapping clones will include an open reading frame. In both instances, complete clones may be identified by comparison with the DNAs and deduced amino acid sequences provided herein.

It is envisaged that the nucleic acid of the invention can be readily modified by nucleotide substitution, nucleotide deletion, nucleotide insertion or inversion of a nucleotide stretch, and any combination thereof. Such mutants can be used e.g. to produce a canine 5T4 mutant that has an amino acid sequence differing from the canine 5T4 sequences as found in nature. Mutagenesis may be predetermined (site-specific) or random. A mutation which is not a silent mutation must not place sequences out of reading frames and preferably will not create complementary regions that could hybridise to produce secondary mRNA structure such as loops or hairpins.

The foregoing considerations may also be applied to the isolation of alternative murine (SEQ. ID. No. 2) or human (SEQ. ID. No. 1) 5T4 antigens.

Administration of Vectors Encoding 5T4

A pharmaceutical composition according to the invention is a composition of matter comprising a vector encoding a 5T4 antigen, as described, as an active ingredient. The active ingredients of a pharmaceutical composition comprising the active ingredient according to the invention ate contemplated to exhibit excellent therapeutic and/or prophylactic activity, for example, in the treatment and/or prophylaxis of tumours or other diseases associated with cell proliferation, infections and inflammatory conditions, when administered in amount which depends on the particular case. Dosage regima may be adjusted to provide the optimum therapeutic response. For example, several divided doses may be administered daily or the dose may be proportionally reduced as indicated by the exigencies of the therapeutic situation.

The active compound may be administered in a convenient manner such as by the oral, intravenous (where water soluble), intramuscular, subcutaneous, intranasal, intradermal or suppository routes or implanting (e.g. using slow release molecules). Depending on the route of administration, the active ingredient may be required to be coated in a material to protect said ingredients from the action of enzymes, acids and other natural conditions which may inactivate said ingredient.

In order to administer the active compound by other than parenteral administration, it will be coated by, or administered with, a material to prevent its inactivation. For example, the active compound may be administered in an adjuvant, co-administered with enzyme inhibitors or in liposomes. Adjuvant is used in its broadest sense and includes any immune stimulating compound such as interferon. Adjuvants contemplated herein include resorcinols, non-ionic surfactants such as polyoxyethylene oleyl ether and n-hexadecyl polyethylene ether. Enzyme inhibitors include pancreatic trypsin.

Liposomes include water-in-oil-in-water CGF emulsions as well as conventional liposomes.

The active compound may also be administered parenterally or intraperitoneally. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), suitable mixtures thereof, and vegetable oils. The proper fluidity can be maintained, for example, by the use of a coating such as lecithin, by the maintenance of the required particle size in the case of dispersion and by the use of superfactants.

The prevention of the action of microorganisms can be brought about by various antibacterial and antifungal agents, for example, parabens, chlorobutanol, phenol, sorbic acid, thirmerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compound in the required amount in the appropriate solvent with various of the other ingredients enumerated above, as required, followed by filtered sterilisation. Generally, dispersions are prepared by incorporating the sterilised active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When the active compound is suitably protected as described above, it may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. The amount of active compound in such therapeutically useful compositions in such that a suitable dosage will be obtained.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavouring agent such as peppermint, oil of wintergreen, or cherry flavouring. When the dosage unit form is a capsule, it may contain, in addition to materials of the above type, a liquid carrier.

Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound may be incorporated into sustained-release preparations and formulations.

As used herein "pharmaceutically acceptable carrier and/or diluent" includes any and all solvents, dispersion media, coatings, antibacterial, and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such as active material for the treatment of disease in living subjects having a diseased condition in which bodily health is impaired.

The principal active ingredients are compounded for convenient and effective administration in effective amounts with a suitable pharmaceutically acceptable carrier in dosage unit form. In the case of compositions containing supplementary active ingredients, the dosages are determined by reference to the usual dose and manner of administration of the said ingredients.

Regimes for administration of 5T4-expressing vectors according to the present invention may be determined by conventional efficacy testing. Especially preferred, however, are regimes which include successive priming and boosting steps. It is observed that such regimes achieve superior breaking of immune tolerance and induction of CTL responses. In a preferred embodiment, the priming step is undertaken using a non-viral vector, such as a plasmid encoding 5T4, whilst boosting is undertaken using a viral vector, such as a poxvirus vector, encoding 5T4 (see Schneider et al., 1998 Nat Med. 4:397-402).

Administration of 5T4 Antigen

In general, approaches outlined above relating to the administration of 5T4-encoding nucleic acids may be used for the administration of 5T4 antigen, as a conventional vaccine preparation, for the therapy and/or prophylaxis of tumours.

In general, vaccines may be prepared 5T4 antigen. The preparation of vaccines which contain an 5T4 as active ingredient(s) is known to one skilled in the art. Typically, such vaccines are prepared as injectables, either as liquid solutions or suspensions; solid forms suitable for solution in, or suspension in, liquid prior to injection may also be prepared. The preparation may also be emulsified, or the protein encapsulated in liposomes. The active immunogenic ingredients are often mixed with excipients which are pharmaceutically acceptable and compatible with the active ingredient. Suitable excipients are, for example, water, saline, dextrose, glycerol, ethanol, or the like and combinations thereof.

In addition, if desired, the vaccine may contain minor amounts of auxiliary substances such as wetting or emulsifying agents, pH buffering agents, and/or adjuvants which enhance the effectiveness of the vaccine. Examples of adjuvants which may be effective include but are not limited to: aluminium hydroxide, N-acetyl-muramyl-L-threonyl-D-isoglutamine (thr-MDP), N-acetyl-nor-muramyl-L-alanyl-D-isoglutamine (CGP 11637, referred to as nor-MDP),N-acetylmurainyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion.

Further examples of adjuvants and other agents include aluminium hydroxide, aluminium phosphate, aluminium potassium sulphate (alum), beryllium sulphate, silica, kaolin, carbon, water-in-oil emulsions, oil-in-water emulsions, muramyl dipeptide, bacterial endotoxin, lipid X, *Corynebacterium parvum* (*Propionobacterium acnes*), *Bordetella pertussis*, polyribonucleotides, sodium alginate, lanolin, lysolecithin, vitamin A, saponin, liposomes, levamisole, DEAE-dextran, blocked copolymers or other synthetic adjuvants. Such adjuvants are available commercially from various sources, for example, Merck Adjuvant 65 (Merck and Company, Inc., Rahway, NJ.) or Freund's Incomplete Adjuvant and Complete Adjuvant (Difco Laboratories, Detroit, Mich.).

Typically, adjuvants such as Amphigen (oil-in-water), Alhydrogel (aluminium hydroxide), or a mixture of Amphigen and Alhydrogel are used. Only aluminium hydroxide is approved for human use.

The proportion of immunogen and adjuvant can be varied over a broad range so long as both are present in effective amounts. For example, aluminium hydroxide can be present in an amount of about 0.5% of the vaccine mixture ($A_2O_3$ basis). Conveniently, the vaccines are formulated to contain a final concentration of immunogen in the range of from 0.2 to 200 µg/ml, preferably 5 to 50 µg/ml, most preferably 15 µg/ml.

After formulation, the vaccine may be incorporated into a sterile container which is then sealed and stored at a low temperature, for example 4° C., or it may be freeze-dried. Lyophilisation permits long-term storage in a stabilised form.

The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkylene glycols or triglycerides; such suppositories may be formed from mixtures containing the active ingredient in the range of 0.5% to 10%, preferably 1% to 2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10% to 95% of active ingredient, preferably 25% to 70%. Where the vaccine composition is lyophilised, the lyophilised material may be reconstituted prior to administration, e.g. as a suspension. Reconstitution is preferably effected in buffer Capsules, tablets and pills for oral administration to a patient may be provided with an enteric coating comprising, for example, Eudragit "S", Eudragit "L", cellulose acetate, cellulose acetate phthalate or hydroxypropylmethyl cellulose.

5T4 may be formulated into the vaccine as neutral or salt forms. Pharmaceutically acceptable salts include the acid addition salts (formed with free amino groups of the peptide) and which are formed with inorganic acids such as, for example, hydrochloric or phosphoric acids, or such organic acids such as acetic, oxalic, tartaric and maleic. Salts formed with the free carboxyl groups may also be derived from inorganic bases such as, for example, sodium potassium, ammonium, calcium, or ferric hydroxides, and such organic bases as isopropylamine, trimethylamine, 2-ethylamino ethanol, histidine and procaine.

Measurement of the Efficacy of 5T4 administration

5T4 activity as an immunotherapeutic molecule may be assessed according to any techniques known in the art, including assays for antibody production, induction of CTL responses and tumour regression models. Exemplary techniques are set forth in the following examples.

The invention is further described, for the purposes of illustration only, in the following examples in which reference is made to the following Figures.

FIG. 1*a* shows a gene construct;
FIG. 1*b* shows a gene construct;
FIG. 2*a* shows a photographic representation;
FIG. 2*b* shows a photographic representation;
FIG. 3*a* present a graph;
FIG. 3*b* present a graph;
FIG. 4*a* presents a graph;
FIG. 4*b* presents a graph;
FIG. 4*c* presents a graph;
FIG. 5 presents a graph;
FIG. 6 presents a graph;
FIG. 7 presents a graph;
FIG. 8 presents a graph; and
FIG. 9 presents a graph;

In slightly more detail:

FIG. 1*a* is a map of recombinant vaccinia virus MVA. Transgenes are placed under the control of the vaccinia virus synthetic early/late promoter. The Lac Z gene is under control of the vaccinia virus 7.5 k early/late promoter. The DNA regions flanking these genes are derived from the deleted region two of MVA, thus allowing homologous recombination into this site.

FIG. 1*b* is a map of the recombinant vaccinia virus WR. The transgenes are under the control of the vaccinia virus synthetic early/late promoter. The Lac Z gene is under control of the vaccinia virus 7.5 k early/late promoter. The DNA regions flanking the genes are derived from the thymidine kinase (tk) gene of Wyeth strain VV, thus allowing recombination into this site.

FIG. 2 shows a western blot of recombinant vaccinia virus expressing human 5T4. Samples are run on a 12% SDS PAGE and transferred to a nitrocellulose membrane.

FIG. 2a: The blot is probed with a 1:500 dilution of MAb 5T4 (anti-human 5T4). Bound antibody is visualised with a anti-mouse HRP conjugated antibody and ECL. Lane 1: recombinant WR clone 1 expressing human 5T4; Lane 2: recombinant WR clone 2 expressing human 5T4; Lane 3: BS-C-1 cells infected with WR; Lane 4: uninfected BS-C-1. cells; Lane 5: B16 melanoma cells; Lane 6: B16 cell line expressing human 5T4.

FIG. 2b: The blot is probed with a 1:500 dilution of rabbit anti-mouse 5T4. Lane 1: recombinant WR expressing LacZ; Lane 2: recombinant WR expressing mouse 5T4; lane 3: recombinant WR expressing human 5T4; lane 4: recombinant MVA expressing mouse 5T4.

FIGS. 3a and 3b are graphs which show that inoculation of mice with MVA-h5T4 Protects against Challenge with CT26 expressing h5T4

FIGS. 4b and 4c are graphs which show that inoculation with MVA-m5T4 induces anti-tumour activity against B16 tumours expressing m5T4.

FIG. 5 is a graph which shows that MVA-h5T4 induces tumour therapy in mice with preestablished lung tumours.

EXAMPLES

Example 1

Figure 1A:
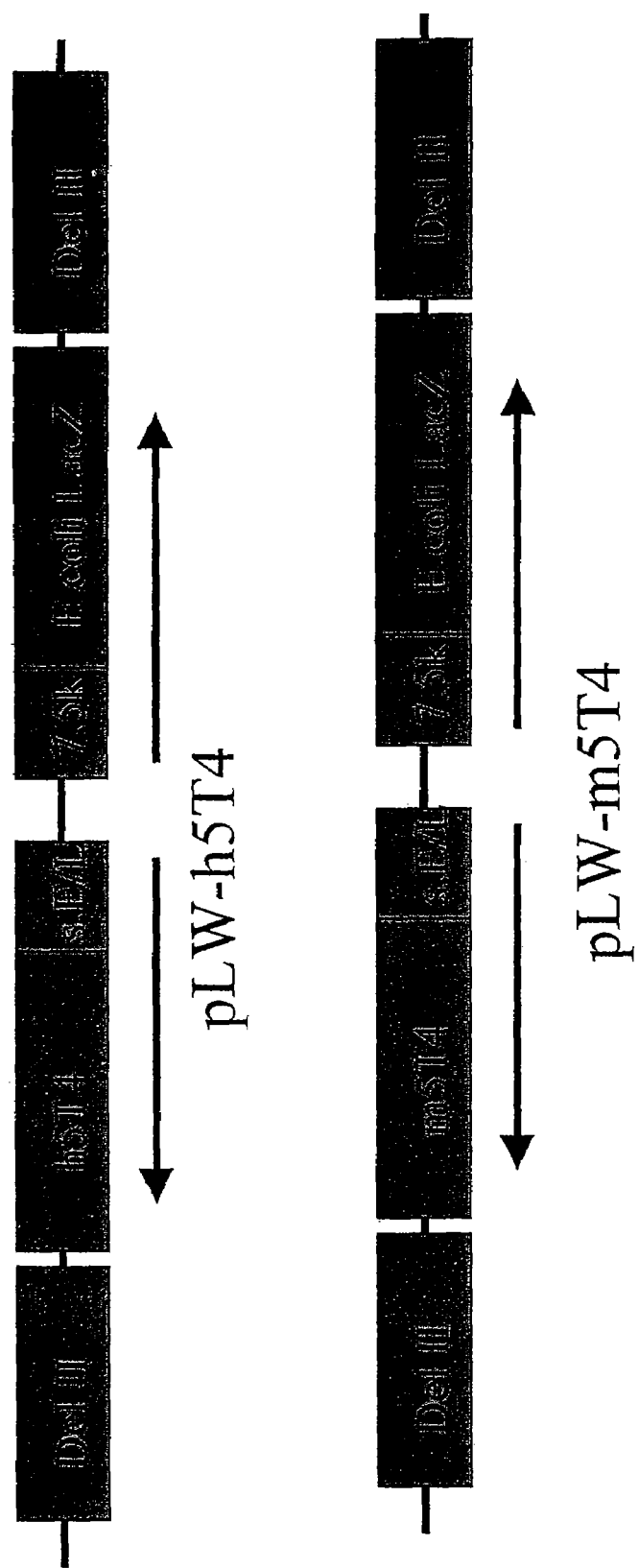
Figure 1B:
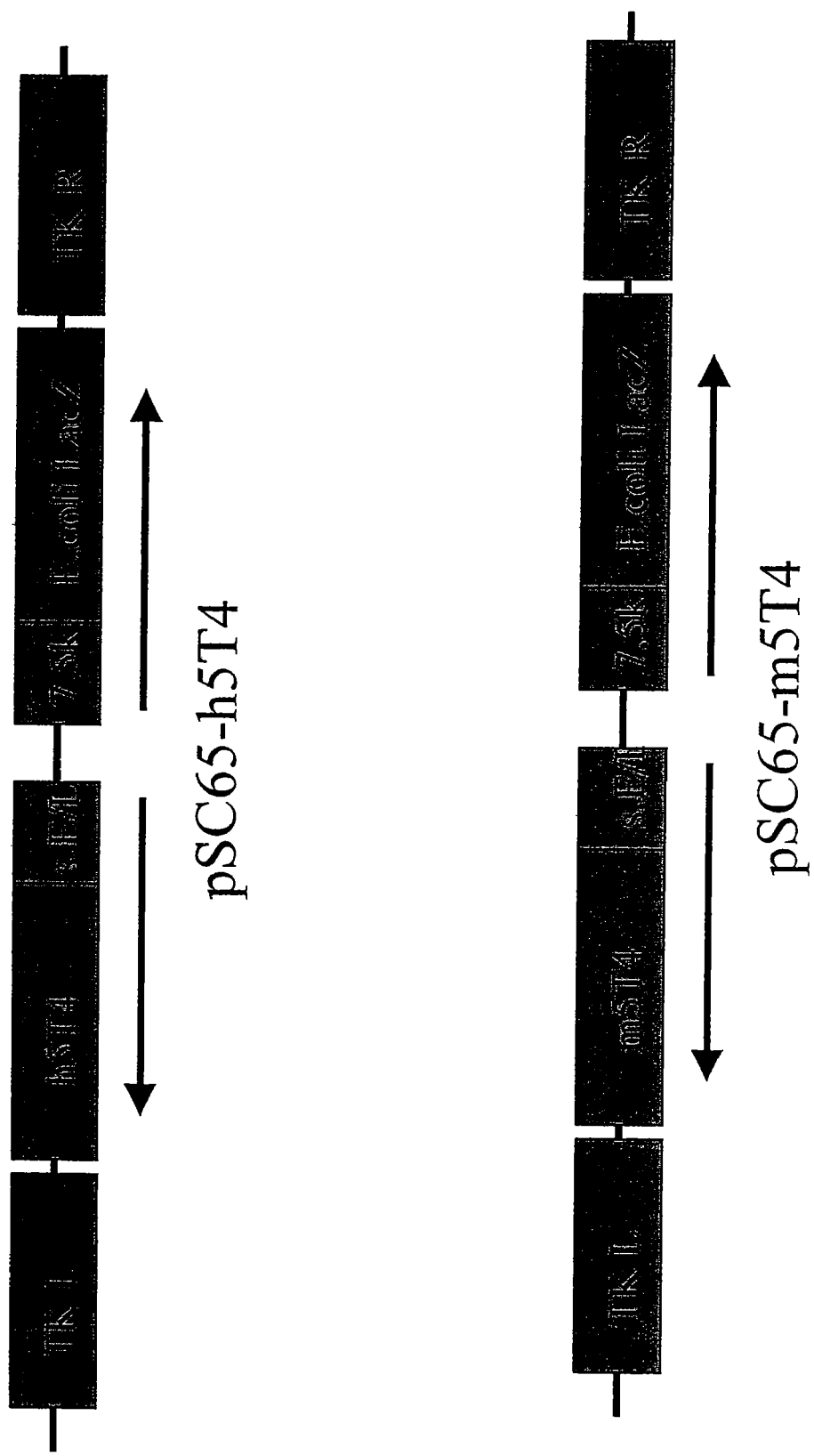

Construction of Recombinant Poxvirus Vectors
Propagation of Vaccinia Virus

The highly attenuated strain MVA is derived from the replication competent strain Ankara and has endured over 570 passages in primary chick embryo fibroblast cells. MVA replication was initially thought to be restricted to CEF cells as only minimal replication in mammalian cells was reported. However, further analysis has shown that Baby Hamster Kidney cells (BHK-21) are able to support high titre production of MVA. MVA may thus be grown on BHK-21 or primary CEF cells (Carroll & Moss (1997) Virology 238:198-211).

To prepare CEF cells, 10 day old chick embryos are gutted and limbs and head are removed before being minced and trypsinised in a solution of 0.25% trypsin and incubation at 37° C. The cell suspension is filtered through a course filter mesh and cells are washed and concentrated by centrifugation at 2000 rpm in a Sorvall RC-3B at 1500 rpm for 5 mins. Cells are suspended in MEM containing 10% FCS, aliquotted into 175 cm flasks and incubated at 37° C. in a $CO_2$ incubator. When monolayers are 95% confluent they are trypsinised and used to seed additional flasks or six well plates. Alternatively, primary cultures are transferred to a 31° C. incubator for later use (Sutter and Moss (1992) Proc Natl Acad Sci USA 89:10847-10851).

Preparation of Crude, Semi-purified and Purified Virus Stocks

Crude virus stocks are prepared for initial recombinant virus analysis or as viral stocks used for subsequent high titre virus preparations. Vaccinia virus preparations can be semi-purified by centrifuging out cell membranes and nuclei or by additional steps involving sucrose centrifugation to prevent contamination by pre-expressed recombinant protein products and cellular organelles. Methods used are a modification of those described by Earl et al., in: Ausubel et al. (Eds.), (1991) Current Protocols in Molecular Biology, pp. 16.16.1-16.16.17, New York: Greene Publishing Associates and Wiley Interscience; Earl and Moss, ibid, pp. 16.17.1-16.17.16; Earl and Moss, ibid, pp. 16.18.1-16.18.10; and Bronte et al., (1997) Proc Natl Acad Sci USA 94(7):3183-3188.

Crude Virus

MVA is grown in either CEF or BHK-21 (obtained from the ATCC) and WR is grown in HeLa or BS-C-1 (ATCC) in 175 $cm^2$ tissue culture flasks. Briefly, confluent monolayers are infected with an moi of approx. 1 pfu with MVA or WR. Virus is suspended in 10ml MEM containing 2% FCS and added to 175 $cm^2$ flasks containing confluent cell monolayers. After inoculation for 1 hour at 37° C. an additional 20 ml MEM containing 2% FCS is added. After 48-72 hours infected cells are scraped into the medium and pelleted at 1500 g for 5 mins. For crude virus preparations cells are resuspended 2 ml MEM (2%) per 175 $cm^2$ flask. Cells are freeze thawed three times, sonicated and aliquotted into 1 ml freezing tubes. A representative aliquot is freeze thawed and titred to determine virus concentration. Virus stocks are stored below –20° C.

Semi-pure Preparations

Infected cells are harvested as described previously (Earl et al.; Earl and Moss; 1991). After centrifugation cells are resuspended in PBS (2 ml/175 $cm^2$ flask) and homogenised by 30-40 strokes in a tight fitting glass dounce homogeniser, on ice. Cell breakage is checked by microscopy. Nuclei, cellular organelles and membranes are removed by a centrifugation at 300 g for 5 mins (4° C.), keep supernatant. The cell pellet is resuspended in 1 ml/175 $cm^2$ flask and centrifugation repeated. The supernatants are pooled, aliquoted and stored.

Purified Preparation

Infected cells are harvested as previously described (Earl et al; Earl and Moss; 1991) and resuspended in 10 mM Tris.Cl, pH 9.0 (2 ml/flask), keeping samples on ice from this point of the procedure. Homogenise as described previously using 10 mM Tris. The lysate is sonicated (on ice) using an XL 2015 sonicating cup (Misonics, USA) at maximum output (500 W) for 1 min. The sample is placed on ice for 1 min and the sonication repeated up to 3 times. A maximum of 5 ml is sonicated at a time, and ice is replenished during sonication. The lysate is gently layered onto a cushion of 17 ml of 36% sucrose (in 10 mM Tris.Cl, pH 9.0) in a SW-27 centrifuge tube. Lyates are centrifuged for 80 mins in an SW-27 rotor at 13 500 rpm(32,900×g), 4° C. The supernatant is discarded and the viral pellet resuspended in sterile PBS and sonicated in a cup sonicator for 1 min (on ice). Concentrated virus is aliquoted and stored at below –20° C.

Example 2

Construction and Characterisation of Recombinant Virus vectors Expressing 5T4

Murine and human 5T4 genes are cloned into WR (pSC65) (Chakrabarti et al., (1997) Biotechniques 23:1094-7) and MVA (pLW22) transfer plasmids to allow homologous recombination into targeted regions of the respective viral genomes.

Recombinant MVA and WR Expressing Human and Murine 5T4

The 1.4 kb murine and human 5T4 (supplied by P. Stern Paterson Institute Manchester) genes are excised from pBSII-m5T4 (pBluescript (Stratagene) containing the 5T4 cDNA) and pBSII-h5T4 (Myers et al., (1994) JBC 269:9319-9324) respectively by Eco RI and Bam HI restriction digestion. The fragments are blunt ended by "filling in" with dNTPs and DNA polymerase. The blunt ended fragments are cloned into the PmeI site of pLW22 (an MVA transfer plasmid, consisting of an early late promoter. (Chakrabarti et al., 1997) upstream of an MCS. Adjacent is a VV 7.5 Kb LacZ cassette, for detection of recombinant virus; see FIG. 1a), and Sma I site of pSC65 (b) (Chakrabarti et al., 1991). pLW22 and pSC65 direct homologous recombination to deletion region II and the tk gene respectively.

In constructs destined for vaccination of human subjects, the LacZ gene under the control of the 7.5 k promoter is omitted. Recombinant plaques are identified by live immunostaining using an anti-5T4 monoclonal antibody, as described previously (Wyatt et al., (1996) Vaccine 14:1451-1458).

Wild type MVA, supplied by B. Moss (NIH, Bethesda, USA) is grown in CEF cells from a plaque purified clone and is the same isolate that was used to make previously described recombinant viruses (Sutter and Moss (1992) Proc Natl Acad Sci USA 89:10847-10851, Sutter et al (1994) Vaccine 12:1032-1040, Hirsch et al (1996) J Virol 70:3741-3752, Carroll and Moss (1995) Biotechniques 19: 352-355, Wyatt et al (1995) Virology 210:202-205, Sutter et al., (1995) FEBS Lett. 371:9-12, Wyatt et al. (1996) Vaccine 14, 1451-1458, Carroll et al (1997) Vaccine, 15:387-394, Carroll and Moss (1997) Virology 238:198-211) The WR stock is supplied by B. Moss (NIH), from the ATCC isolate (see e.g. Earl and Moss, 1991). The WR stock is prepared in HeLa S3 cells (ATCC).

The protocol used to make recombinant MVA virus is similar to that described previously (Carroll & Moss (1997) Virology 238:198-211). Briefly: BHK-21 or CEF cells are infected at an moi of 0.1 with an MVA stock Plasmid DNA is diluted to 2 µg in 100 ul d.H$_2$O and mixed with 30 µg lipofectin (BRL) diluted to 100 µl with sterile d.H2O. After 10 minutes incubation at RT the Lipofectin/DNA solution is added to infected cells overlaid with Opti MEM. Five hours after incubation at 37° C. cells media is aspirated and replaced with MEM containing 2% FCS. Cells are harvested after a further 36 hours incubation and assayed for the expression of β-gal on CEF or BHK-21 cells in the presence of 5-bromo-3-indolyl-D-galactosidase. Isolated plaques are plaque purified at least an additional 3 times. After plaque purification small viral stocks are prepared in CEF or BHK-21 cells.

Protocols for the construction of recombinant WR are similar to those described previously (Carroll and Moss (1995) Biotechniques 19: 352-355; Earl and Moss, 1991). Briefly: recombination is carried out as for MVA. However, BS-C-1 cells are used and recombinant plaques assayed in 143B tk$^-$ cells in the presence of BrdU with an agar overlay containing the substrate for the LacZ gene, 5-bromo-3-indolyl-D-galactosidase. Neutral red is used to detect LAC Z negative spontaneous tk$^-$ virus for evaluation of virus homogeneity.

Figure 2A:
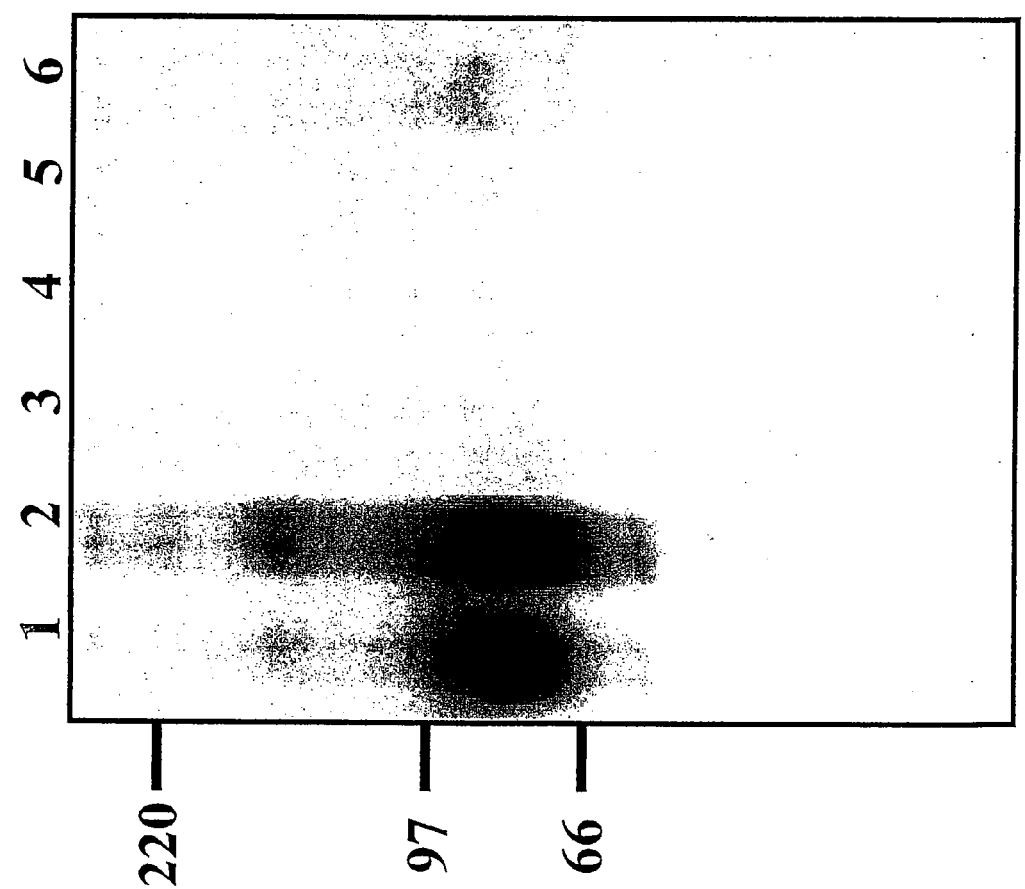
Figure 2B:
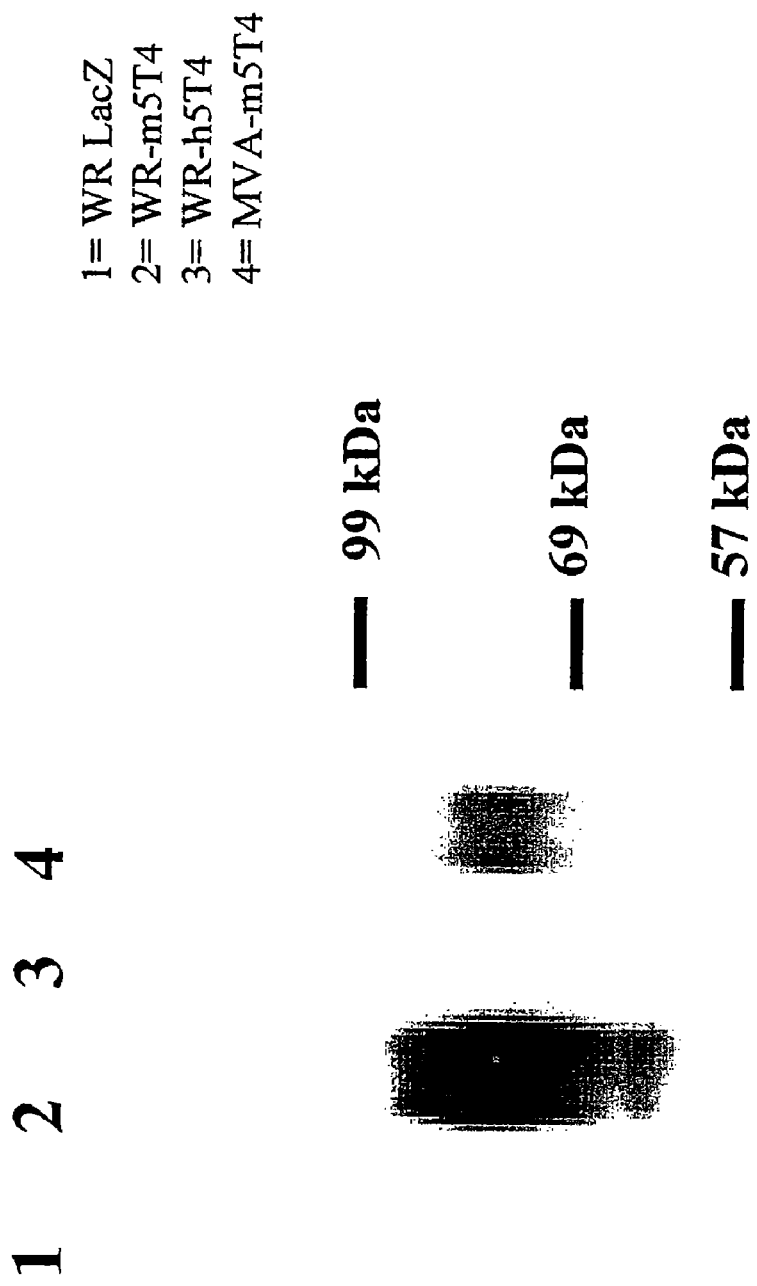

Recombinant protein expression is initially analysed by direct plaque immunostaining using antibodies specific for h5T4 and m5T4 using a method similar to that described previously (Carroll & Moss (1997) Virology 238:198-211). Briefly: recombinant viruses are plaqued on monolayers of BS-C-1 cells, fixed with acetone/methanol and treated with MAb 5T4 (Hole N, and Stern P L, (1990) Int J Cancer 45(1): 179-184). Anti-mouse HRP conjugated antibody and dianizidine substrate are used to visualise recombinant 5T4 protein expression. 5T4 expressed protein is further characterised by western blotting under non-reducing conditions, as the MAb recognises a conformational epitope. As can be seen in FIG. 2 recombinant viruses express high levels of protein at the appropriate size of 72 kDa. The stock is checked for homogeneity by double-immunostaining as described in Carroll & Moss (1997) Virology 238:198-211.

Example 3

Animal Models to Illustrate Immunological Cross Protection of Mouse 5T4 with Human 5T4.

To determine if the 5T4 gene product from one species can induce immunity to 5T4 in another species, the recombinant poxviruses are tested in murine tumour models. The mouse models are based on CT26, a chemically induced adenocarcinoma of BALB/c origin (Brittain et al., (1980) Cancer Res. 40:179-184), and on B16, a melanoma line derived from C57 B6 mice. Both the CT26 line and B16 are stably transformed to express human and murine 5T4. Mice are injected I.V. (to induce lung nodules, CT26) or subcutaneously (CT26 and B16) to make single mass subcutaneous tumours. Groups of 7 BALB/c mice were inoculated three times IV or IM with 1×10$^7$ pfu of MVA-h5T4 (here the 5T4 antigen is called OBA1) construct on days 0, 21 and 42. Mice were then challenged IV with 5×10$^5$ tumour cells that were stably transfected with human 5T4. 14 days after challenge mouse lungs were removed and lung nodules counted.

Results 3

Figure 3B:
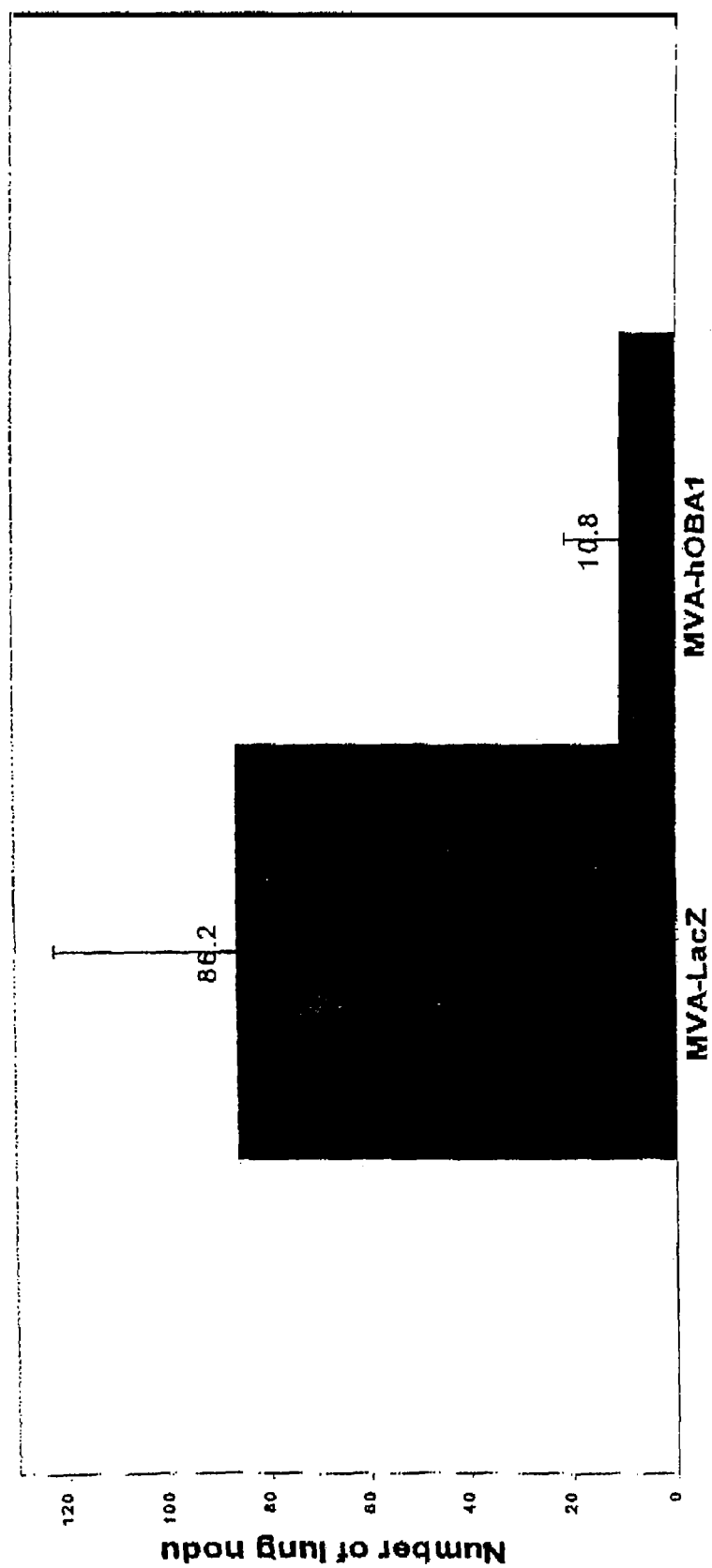

The results shown in FIGS. 3a and 3b demonstrate that mice vaccinated with MVA-h5T4 showed anti-tumour activity when challenged with the syngeneic tumour line CT26 expressing the h5T4 protein. Mann-Whitney statistical analysis show that protection after vaccination with MVA-h5T4 is significant, compared to vaccination with MVA-LacZ or PBS (p<0.05).

Example 4

Groups of 5 C57 BL 6 mice were inoculated twice at a three week interval with 10$^7$ pfu of MVA-h5T4 (IV or IM) or MVA-Lac Z (IV). Mice were challenged with 5×10$^5$ B16-h5T4 cells. Tumours sizes were recorded at 2 day intervals post tumour challenge. Individual tumour areas are given.

Groups of 5 and 7 C57 BL 6 mice were inoculated twice at a three week interval with 10$^7$ pfu of MVA-m5T4 (IV or IM) or MVA-Lac Z (IV). Mice were challenged with 5×10$^5$ B16-m5T4 cells. Tumours sizes were recorded at 2 day intervals post tumour challenge. Individual tumour areas are given.

Results 4

Figure 4A:
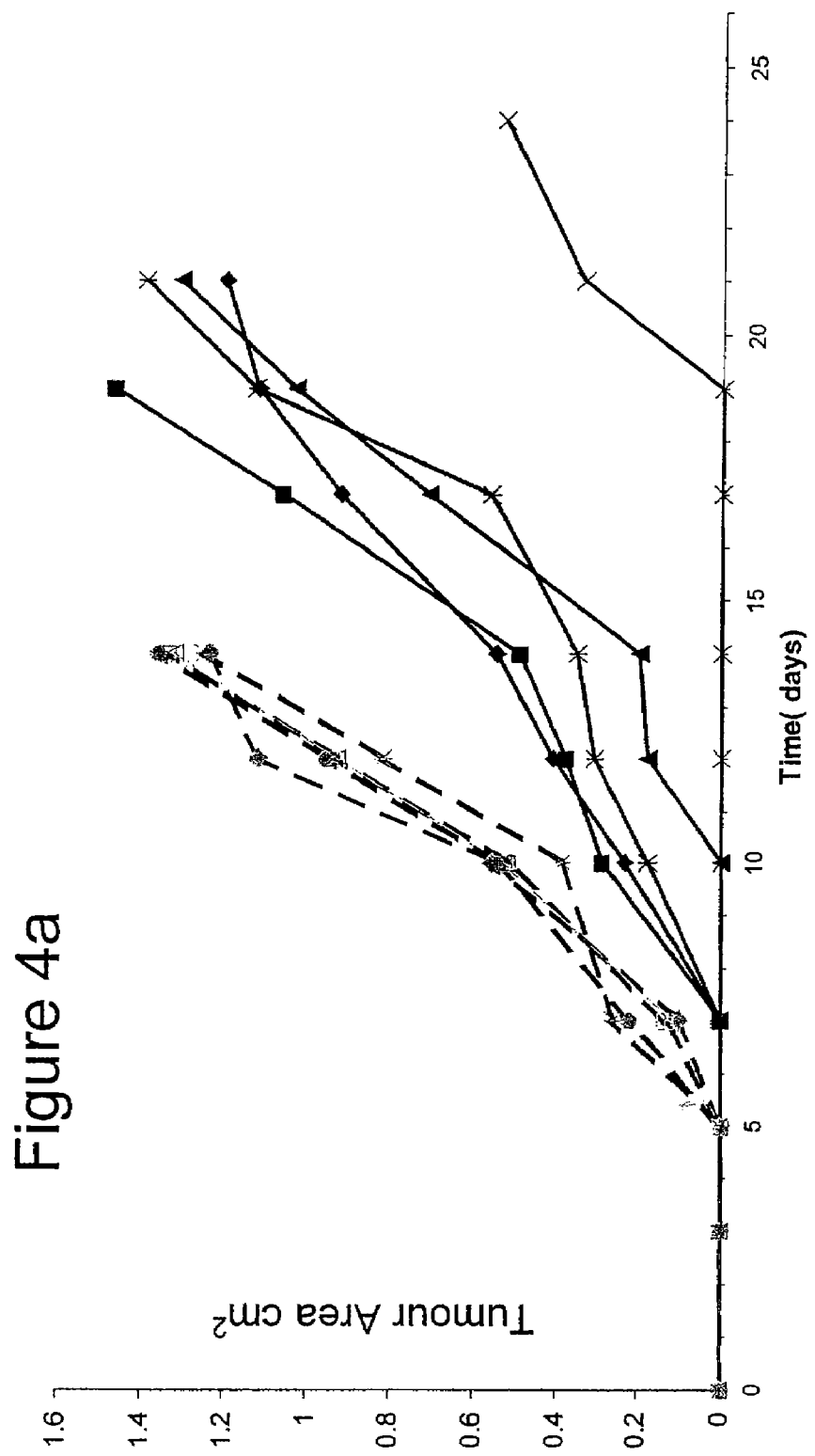
FIG. 4a is a graph which shows that inoculation with MVA-h5T4 induces anti-tumour activity against B16 tumours expressing h5T4.

FIG. 4a shows that vaccination with MVA-h5T4 clearly has an anti-tumour effect when mice are challenged with B16-h5T4. Mann-Whitney statistical analysis of data in FIG. 4a demonstrates that tumour retardation after vaccination with MVA-h5T4 is significant, compared to vaccination with MVA-LacZ (p<0.05).

Figure 4B:
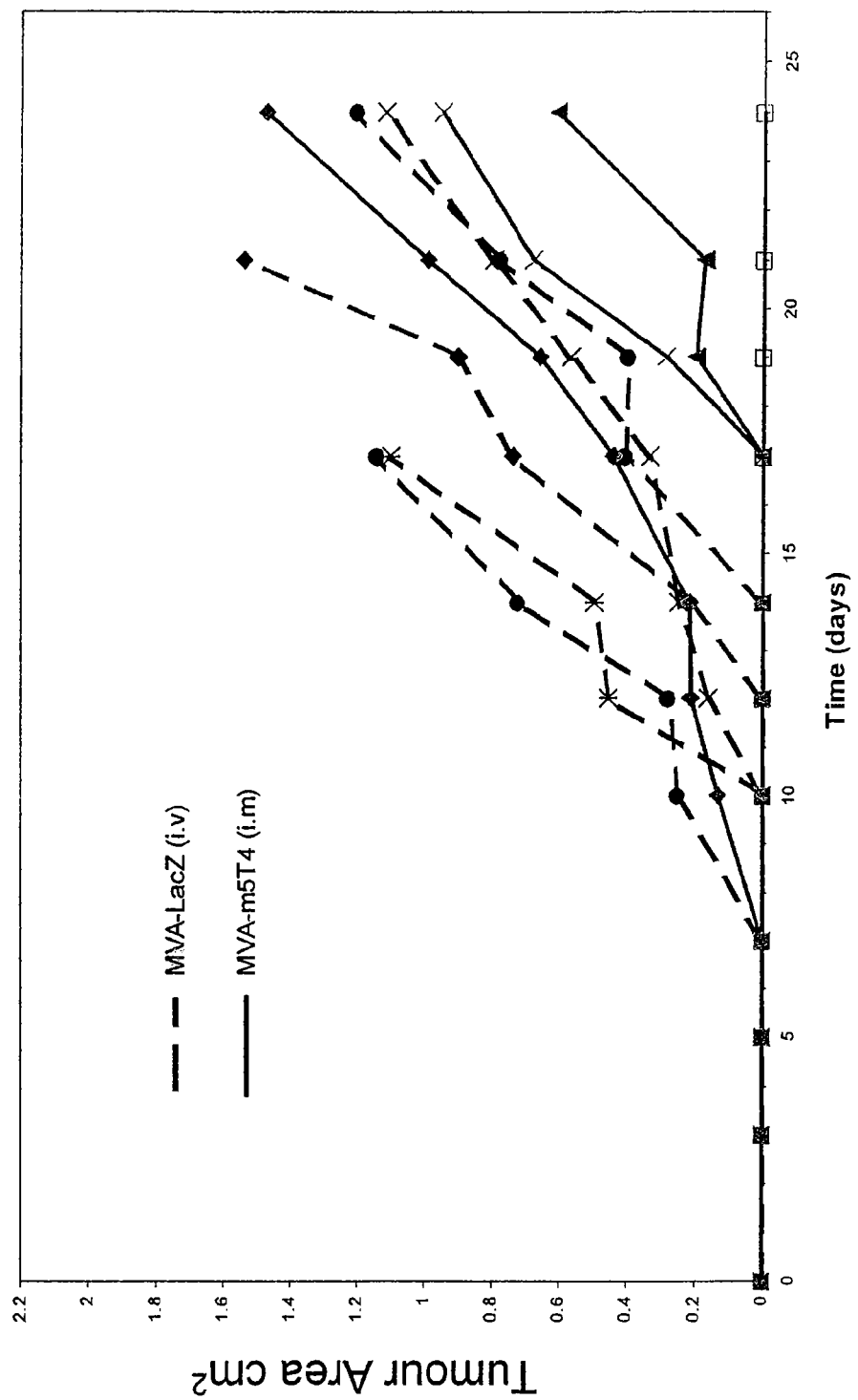

FIGS. 4b and 4c show that vaccination with MVA-m5T4 clearly has an anti-tumour effect when mice are challenged with B16-m5T4. Mann-Whitney statistical analysis of data in FIG. 4c demonstrates that tumour retardation after vaccination with MVA-m5T4 is significant, compared to vaccination with MVA-LacZ (p<0.05).

Example 5

Female BALB/c mice were injected IV with 5×10⁵ CT26-h5T4 cells. After 3 days macro lung tumours establish. Mice were treated on day 3 and 10 post tumour inoculation with 10⁷ pfu of MVA-Lac Z, MVA-h5T4 (groups of 10 mice) or PBS (group of 5 mice). Lungs are stained and tumours counted 14 days post tumour inoculation.

Results 5

It is clear from FIG. 5 that treatment with MVA-h5T4 has a significant therapeutic effect on established CT26 lung nodules expressing h5T4. Statistical analysis (Mann-Whitney) shows that therapy with MVA-h5T4 is significant when compared to MVA-Lac Z or PBS (p<0.05).

Example 6

CT26-m5T4 and B16-m5T4 Self Antigen Model

C57 BL6 mice are inoculated I.V. twice at a three week interval with 1×10⁷ pfu of either MVA-LacZ (n=3) or MVA-m5T4 (n=6). Three weeks after the last vaccination mice are challenged S.C. with 5×10⁵ B16 expressing m5T4. Development of sub cutaneous (S.C.) tumours is monitored.

Figure 6:
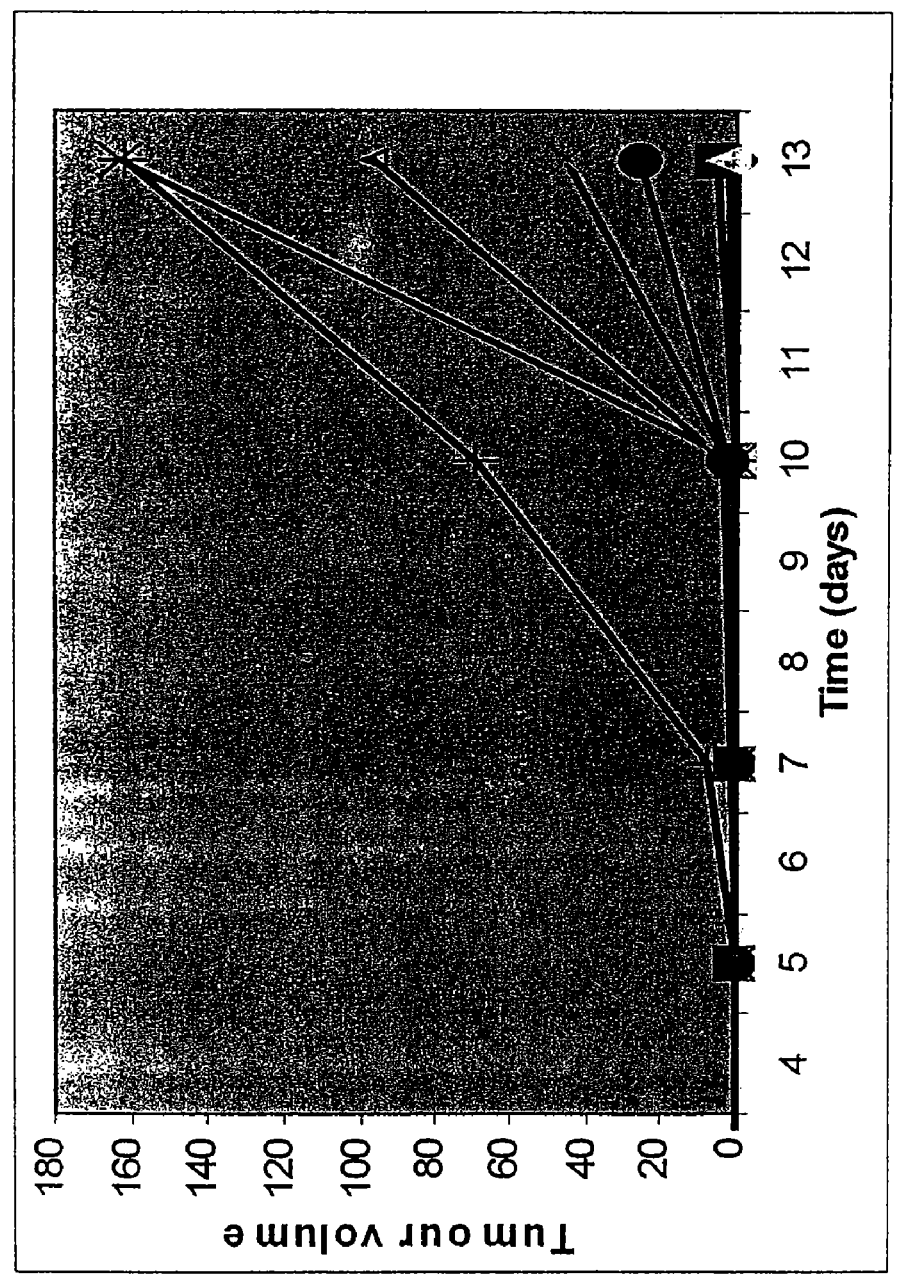
FIG. 6 is a graph which shows that mice that are vaccinated with MVA-m5T4 develop tumours at a slower rate than those that receive the control vaccine.

FIG. 6 shows that mice that are vaccinated with MVA-m5T4 develop tumours at a slower rate than those that receive the control vaccine. Additionally, the tumours in the m5T4 vaccinated mice are on average 5 fold smaller in volume (10 fold smaller by day 13) compared to those mice that receive the MVA-LacZ treatment. This protective property can be paralleled by the m5T4 antibody response induced in these mice.

Example 7

BALB/c mice are inoculated I.V. twice at a three week interval with 1×10⁷ pfu of either MVA-LacZ (n=5) or MVA-m5T4 (n=6). Three weeks after the last vaccination mice are challenged with 5×10⁵ CT26 expressing m5T4. 12 days after challenge mouse lungs are removed and tumour nodules counted in a blinded manner. Results 7

Figure 7:
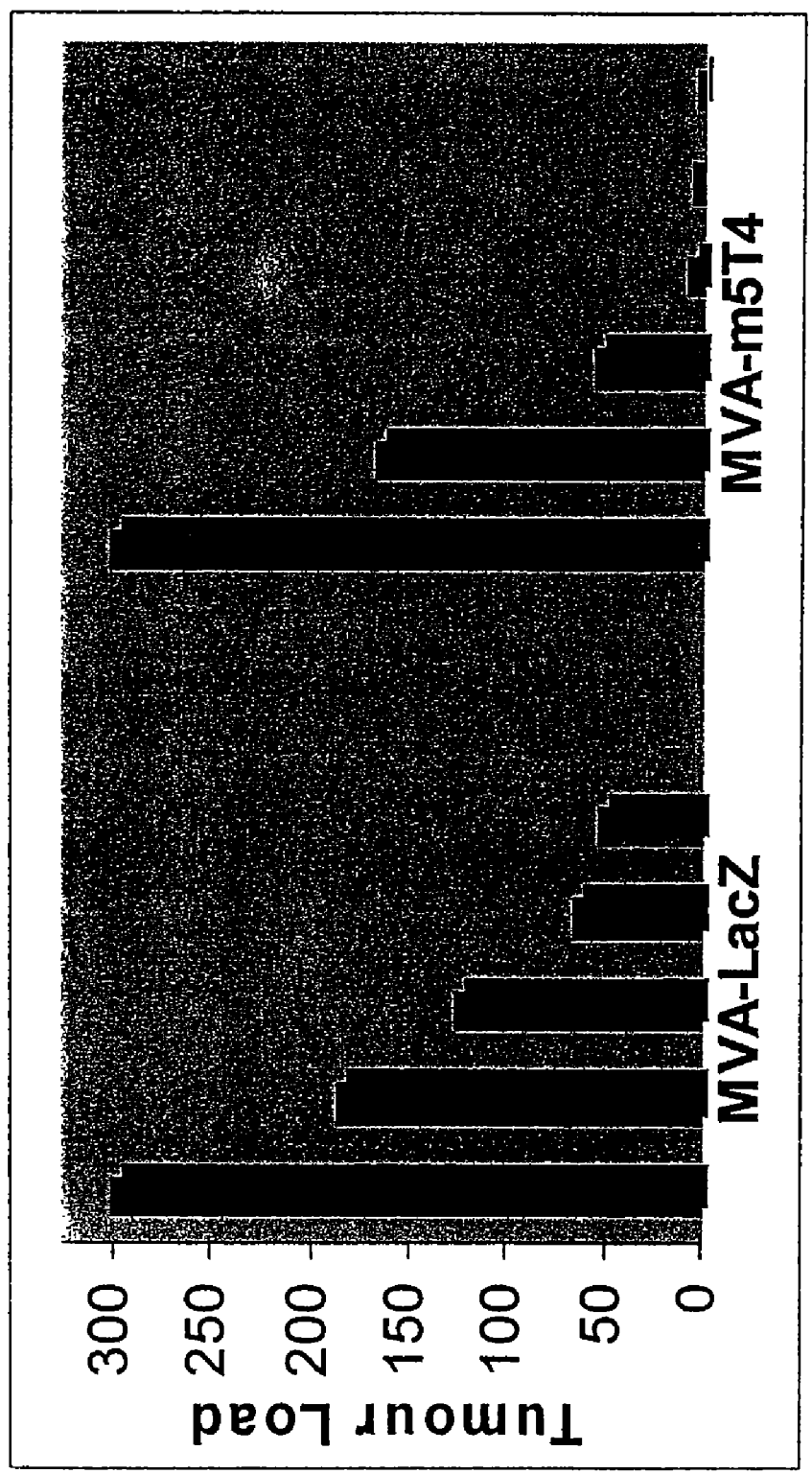
FIG. 7 is a graph which shows that mice that were vaccinated with MVA-m5T4 had a lower tumour burden than those mice that received MVA-LacZ treatment.
Figure 8:
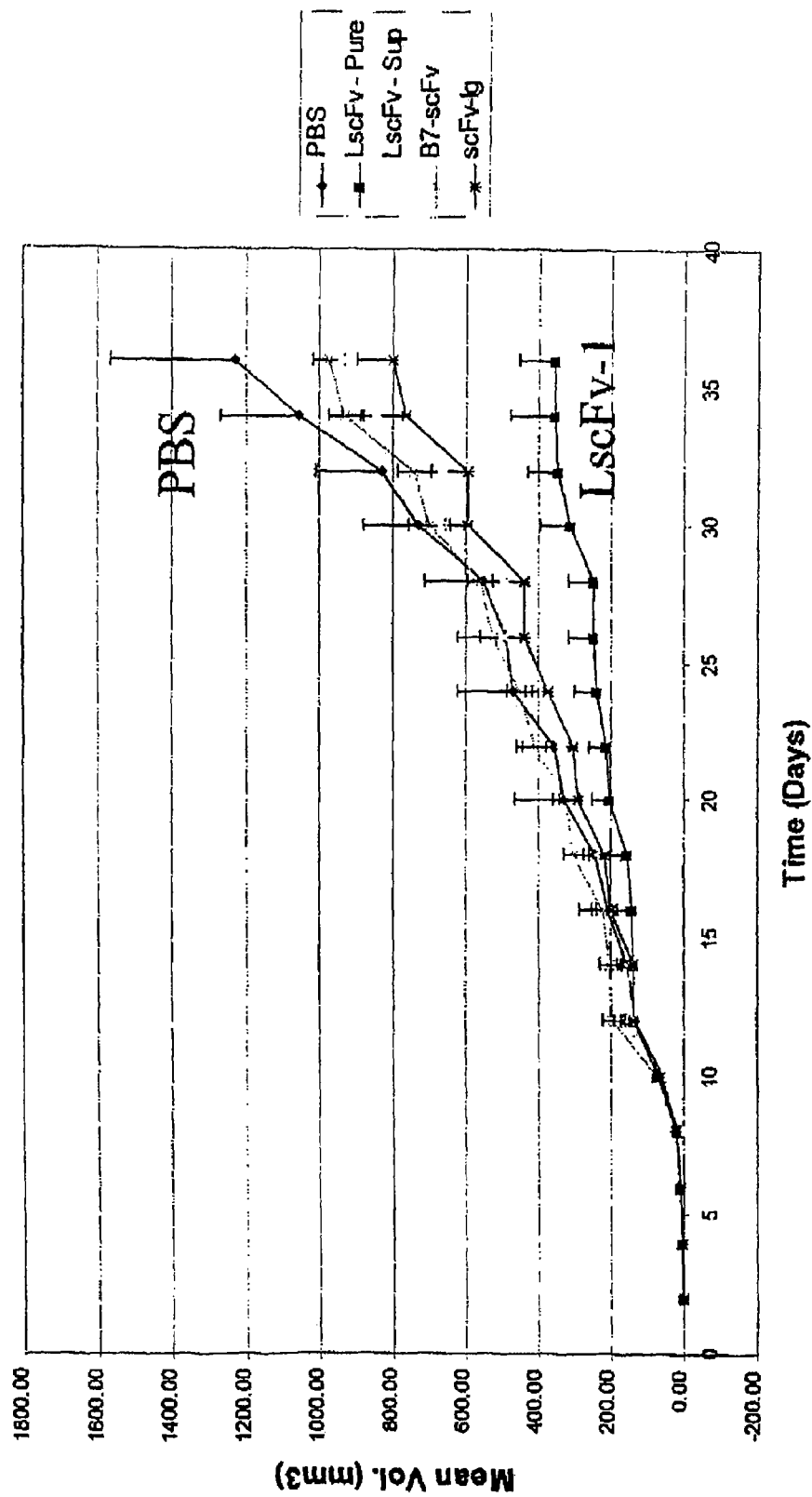
Figure 9:
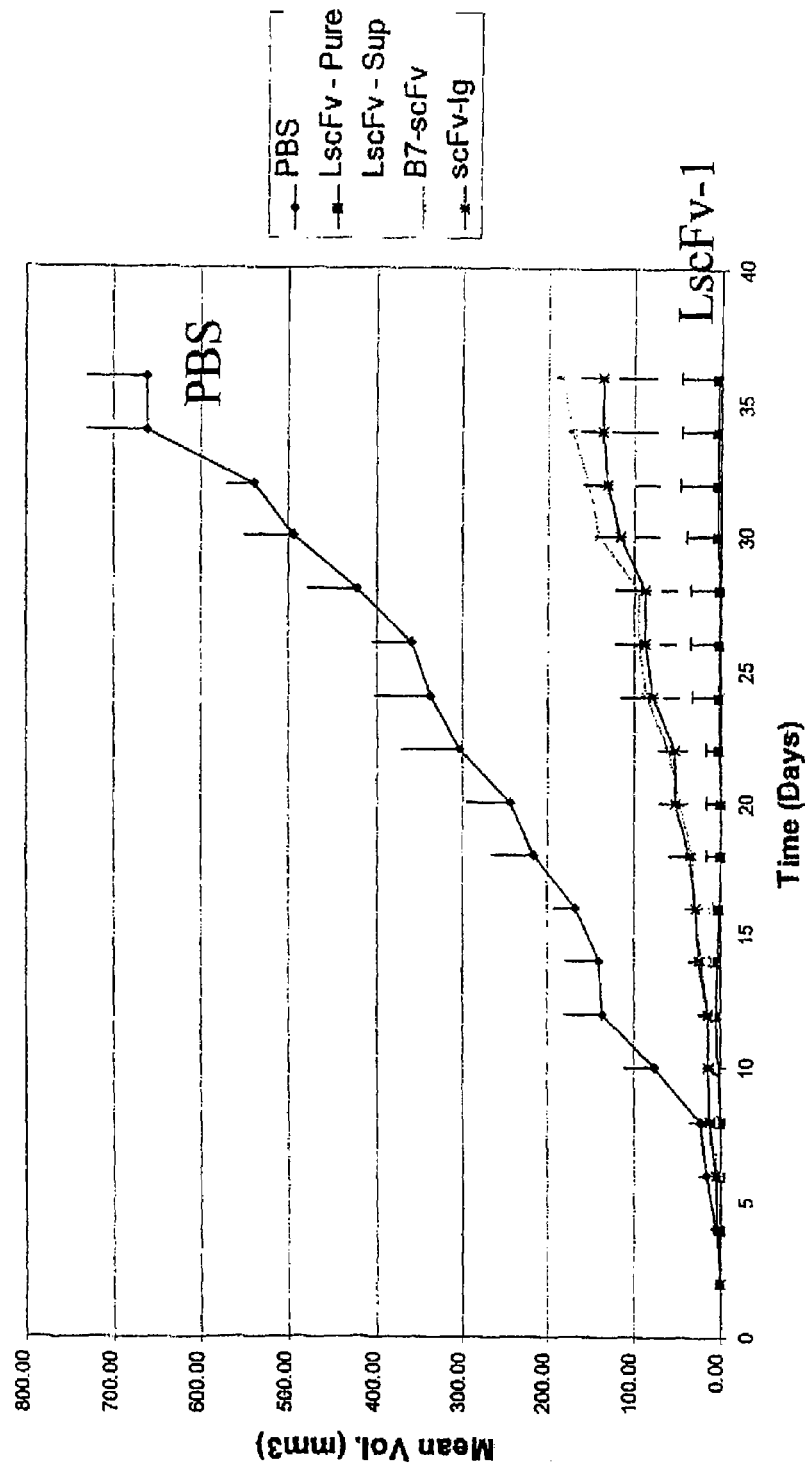

FIG. 7 shows that mice that were vaccinated with MVA-m5T4 had a lower tumour burden than those mice that received the MVA-LacZ treatment. This protective property can be paralleled by the m5T4 antibody response induced in these mice.

Example 8

Induction of 5T4 Antibody Responses in C57 and BALB/c Mice

Mice are vaccinated as above with MVA-m5T4 and MVA-h5T4, and bled 10 days after each vaccination.

Results 8

MVA-m5T4 is able to overcome tolerance in both BALB/c and C57 B16 mice, after two inoculations. Additionally, mice primed with DNA followed by MVA do not show signs of an antibody response to m5T4.

It is therefore shown, in two murine tumour models, that vaccination with MVA expressing murine 5T4 has protective properties against syngeneic tumour cells expressing m5T4. These anti-tumour properties can be paralleled to the anti-m5T4 immune response (measured by ELISA). Additionally, it is shown that the induction of such an immune response does not induce auto immune toxicity in these animals.

Example 9

Immune Response to 5T4 Using Primer Boost Vaccination

In order to evaluate the efficacy of MVA and naked DNA vectors to induce immunity to 5T4 in BALB/c and C57 BL6 mice, mice are inoculated using successive priming and boosting with both naked DNA and MVA vectors encoding mouse and human 5T4. In more detail, mice are inoculated with 1×10⁷ pfu of MVA-5T4 i.v., 50 g pCl-h5T4 (25 g/hind leg) or 25 g pCl-m5T4 (12.5 g/hind leg) on day 0, with a second (booster) inoculation on day 21 with MVA-5T4. On day 29 the mice are bled and antibody titres determined by ELISA.

Results 9

The following titres (defined as that dilution giving an OD above twice the background OD of MVA-LacZ) as shown in Tables 2 and 3 are observed:

TABLE 2

Murine 5T4 Antibody Titres from Mice Inoculated with MVA and DNA vectors expressing human and murine 5T4

| Mouse Strain | MVA-m5T4 | pCl-m5T4 | MVA-h5T4 | pCl-h5T4 |
|---|---|---|---|---|
| Antibody Titre | MVA-m5T4 | MVA-m5T4 | MVA-h5T4 | MVA-h5T4 |
| BALB/c | 1:10 000 | <1:1 000 | <1:1 000 | <1:1 000 |
| C57 BL6 | 1:16 000 | <1:1 000 | <1:1 000 | <1:1 000 |

TABLE 3

Human 5T4 Antibody Titres from Mice Inoculated with MVA and DNA vectors expressing human and murine 5T4.

| Mouse Strain | MVA-m5T4 | pCl-m5T4 | MVA-h5T4 | pCl-h5T4 |
|---|---|---|---|---|
| Antibody Titre | MVA-m5T4 | MVA-m5T4 | MVA-h5T4 | MVA-h5T4 |
| BALB/c | 1:5 000 | <1:1 000 | >1:32 000 | 1:32 000 |
| C57 BL6 | 1:4 000 | <1:1 000 | >1:32 000 | >1:32 000 |

The results show that use of either DNA:MVA prime:boost with a heterologous 5T4 antigen (h5T4) or an MVA:MVA prime:boost with heterologous or homologous 5T4 (HST4 or m5T4) is effective in raising a high titre of antibodies.

Example 10

Modified Forms of 5T4 for Cancer Immunotherapy

It is possible to modify human 5T4 to enhance its immunogenicity and thus induce more efficacious immunotherapy responses. To do this, identification of HLA CTL epitopes and modification of such epitopes to improve binding to the HLA molecule, and thus more efficient CTL induction, is performed using program "Peptide Binding Predictions" devised by K. Parker and the National Institute of Health; on the world wide web at bimas.dcrt.nih.gov/cgibin1molbio/kenparkercomboform (see Parker et al., J. Immunol., 152:163 (1994)). The following results are obtained for human (Table 4) and murine (Table 5) 5T4 9mers:

TABLE 4

Human 5T4 9mers binding to HLA A 0201

| Rank | Start | Sequence | Dissociation Time |
|---|---|---|---|
| 1 | 97 | FLTGNQLAV (SEQ ID NO: 5) | 319.939 |
| 2 | 364 | ALIGAIFLL (SEQ ID NO: 6) | 284.974 |

TABLE 4-continued

Human 5T4 9mers binding to HLA A 0201

| Rank | Start | Sequence | Dissociation Time |
|---|---|---|---|
| 3 | 351 | SLQTSYVFL (SEQ ID NO: 7) | 176.240 |
| 4 | 368 | AIFLLVLYL (SEQ ID NO: 8) | 137.482 |
| 5 | 283 | GLPHIRVFL (SEQ ID NO: 9) | 117.493 |
| 6 | 358 | FLGIVLALI (SEQ ID NO: 10) | 110.379 |
| 7 | 81 | NLTEVPTDL (SEQ ID NO: 11) | 87.586 |
| 8 | 95 | NLFLTGNQL (SEQ ID NO: 12) | 79.041 |
| 9 | 222 | FLYLPRDVL (SEQ ID NO: 13) | 63.174 |
| 10 | 373 | VLYLNRKGI (SEQ ID NO: 14) | 56.754 |
| 11 | 365 | LIGAIFLLV (SEQ ID NO: 15) | 30.890 |
| 12 | 290 | FLDNNPWVC (SEQ ID NO: 16) | 28.109 |
| 13 | 301 | HMADMVTWL (SEQ ID NO: 17) | 27.207 |

TABLE 5

Murine 5T4 binding to human HLA A 0201

| Rank | Start | Sequence | Dissociation Time |
|---|---|---|---|
| 1 | 307 | YMADMVAWL (SEQ ID NO: 18) | 3680.892 |
| 2 | 81 | NLLEVPADL (SEQ ID NO: 19) | 324.068 |
| 3 | 97 | FLTGNQMTV (SEQ ID NO: 20) | 319.939 |
| 4 | 370 | ALIGAIFLL (SEQ ID NO: 21) | 284.974 |
| 5 | 228 | FLFLPRDLL (SEQ ID NO: 22) | 178.158 |
| 6 | 357 | SLQTSYVFL (SEQ ID NO: 23) | 176.240 |
| 7 | 374 | AIFLLVLYL (SEQ ID NO: 24) | 137.482 |
| 8 | 289 | GLAHVKVFL (SEQ ID NO: 25) | 117.493 |
| 9 | 364 | FLGIVLALI (SEQ ID NO: 26) | 110.379 |
| 10 | 379 | VLYLNRKG (SEQ ID NO: 27) | 56.754 |

Example 11

Mutation of H5T4 to Improve Binding of HLA A0201

The above data derived from the Parker Peptide Binding Predictions Programme indicates that mutation of the human AA sequence starting at position 301 from YMADMVAWL (SEQ ID NO: 18) when changed to HMADMVTWL (SEQ ID NO: 17) leads to a 10 fold increase in halftime of dissociation to HLA A0201. This increased binding affinity greatly improves the CTL induction properties of 5T4 polypeptides (see also Overwijk et al., 1998 J. Exp. Med. 188:277-86).

Results 11

Additionally, mutations in the h5T4 9mer starting at 81 from NLTEVPTDL (SEQ ID NO:11) to NLLEVPADL (SEQ ID NO:19) lead to a 4 fold increase in the dissociation half time of the 9mer to HLA A 0201.

Example 12

Toxicity Studies

Absence of Autoimmune Toxicity

The purpose of this study was to study the possible effects of inducing autoimmune toxicity against 5T4 in the murine model Experimental Design Groups of 5 BALB/c and C57 BL6 mice were inoculated IV with $10^7$ pfu of recombinant vaccinia virus MVA expressing human (MVA-h5T4) and murine 5T4 (MVA-m5T4). As a negative control mice were inoculated with MVA expressing *E. Coli* LacZ (MVA-LacZ) or PBS.

Female BALB/c mice were inoculated a total of four times over an 14-month period. C57 BL6 mice were inoculated 3 times over an 14 month period. Blood samples were taken after inoculation and evaluated for 5T4 specific antibody by ELISA.

Results 12a

Antibody response: After 2 inoculations mice inoculated with MVA-m5T4 and MVA-h5T4 had high levels of anti-m5T4 and anti-h5T4 respectively, in their serum (see Table 2 and Table 3).

Toxicity: Mice were observed for signs of ill health on a daily basis. At no time during the past 14 months did the physical appearance of animals inoculated with MVA-m5T4 or MVA-h5T4 differ from those animals inoculated with MVA-Lac Z or PBS. Two reports on the health of the animals, prepared by a qualified veterinarian, were prepared that states all animals appear healthy.

Summary

Groups of BALB/c and C57 BL6 mice were inoculated up to four times over an 14 month period with MVA expressing m5T4 (MVA-m5T4) or MVA expressing h5T4 (MVA-h5T4) antigens and checked for signs of toxicity. Though mice were shown to have high titres of antibodies to m5T4 there were no signs of ill health over the 14-month period. A qualified veterinarian has assessed animals and found them to show no signs of ill health, indicating an absence of auto immune toxicity.

Thus, inoculation of BALB/c or C57 BL6 mice with MVA-h5T4 or MVA-m5T4 induces an antibody response to h5T4 and m5T4 respectively. Such a response has no detrimental effect on the health of the mice.

Example 12b

Effects of 5T4 Auto-immunity on Fertility

5T4 is found on human and murine placenta. Accordingly, is possible that an anti mouse 5T4 immune response may prevent mice becoming pregnant or effect the health of the foetus. We carried out extensive studies to address these issues. The purpose of this study was to assess the effects of an immune response in both BALB/c and C57 BL6 female mice to m5T4 on pregnancy.

Experimental Design

Groups of 5 female BALB/c and C57 BL6 mice were inoculated on three occasions IV with $10^7$ pfu of MVA-m5T4, MVA-LacZ or PBS. At specific times following the final inoculations (day 10, 30 and 60) mice were mated and evaluated for their ability to become pregnant and give birth to healthy pups.

Results 12b (i) C57 BL6 Mouse Study

TABLE 6

| 10 DAY Study | | | |
|---|---|---|---|
| | MVA-m5T4 × 3 | MVA-LacZ × 3 | PBS |
| No. of pregnancies | 4/5 = 80% | 4/5 = 80% | 3/5 = 60% |
| No. Live births | 24 | 30 | 18 |
| Average litter size | 6 | 7.5 | 6 |

TABLE 7

| 30 DAY Study | |
|---|---|
| | MVA-m5T4 × 3 |
| No. of pregnancies | 4/5 = 80% |
| No. Live births | 22 |
| Average litter size | 5.5 |

TABLE 8

60 DAY Study

| | MVA-m5T4 × 3 |
|---|---|
| No. of pregnancies | 5/5 = 100% |
| No. Live births | 33 |
| Average litter size | 6.6 |

(ii) BALB-c Mouse Study

TABLE 9

10 DAY Study

| | MVA-m5T4 × 3 | MVA-LacZ × 3 | PBS |
|---|---|---|---|
| No. of pregnancies | 5/5 = 100% | 4/5 = 80% | 4/5 = 80% |
| No. Live births | 30 | 23 | 22 |
| Average litter size | 6 | 5.75 | 5.5 |
| No. surviving to weaning | 24 = 80.0% | 19 = 82.6% | 22 = 100% |
| Ratio F:M | 13:11 | 14:5 | 11:11 |
| Average weights | 10.4 g | 11.2 g | 10.1 g |

TABLE 10

45 DAY Study

| | MVA-m5T4 × 3 |
|---|---|
| No. of pregnancies | 4/4 = 100% |
| No. Live births | 24 |
| Average litter size | 6 |
| No. surviving to weaning | 24 = 100.0% |
| Ratio F:M | 15:9 |
| Average weights | 11.4 g |

Summary

BALB/c and C57 BL6 mice were injected with an MVA recombinant virus expressing m5T4 and an anti-m5T4 antibody response was induced. These mice were mated and were shown to get pregnant and give birth to pups at the same rate as mice that were vaccinated with a control virus (see tables 6-10) Additionally, there was no effect on the health of the pups to weaning. Thus, inoculation with MVA-m5T4 and induction of m5T4 antibody response does not have a detrimental effect on (i) Fertility of BALD/c and C57 BL6 mice; (ii) Number of live births and (iii) Weight and survival of pups to weaning.

Example 12c

Distribution of 5T4 in Normal Human Tissues

The purpose of this study was to carry out an independent evaluation of 5T4 distribution in normal human tissues. Some past studies have suggested that normal tissue expressing 5T4 could potentially be a target for an immune response induced against this tumour antigen even though the level of 5T4 expression in normal tissue associated with small vessels was found to be over 1000-fold lower than that associated with placenta. It was not clear whether the staining was specific or reflected some cross reactivity by the MAb.

Experimental Design

Slide preparations of thirty two different tissue types from 3 different donors were evaluated by a qualified pathologist under GLP conditions. Cryosections of each tissue sample were stained with three different concentrations of Mab specific for 5T4.

Results 12c

The summary Table 11 indicates that tissue sections from all essential organs including: brain, CNS, liver and kidney were negative for 5T4 expression. Some weak staining in one or more of the donor tissues was evident in several non-essential tissues. It should be noted that some of the positive staining was observed in tissues derived from individuals that had died from cancer.

Although past studies using immunohistochemical analysis have revealed that some 5T4 staining was observed in "some small vessels" of some non-cancerous organs which "appeared to be weakly staining" and include; Kidney (glomeruli), bladder (epithelium), small intestine (villous epithelium), uterus (endometril glands), cervix (endocervical glands) and skin (basal epidermis), this independent study shows that 5T4 is not expressed on cells of essential organs, furthermore, expression in some normal tissues is at a low level and is sporadic as it is rarely seen in all three donor samples. Thus, this data indicates that 5T4 tissue expression is more stringently restricted compared to some other tumour antigens that have been employed in tumour immunotherapy trials. Therefore these findings reiterate the view that 5T4 is an excellent candidate antigen for cancer immunotherapy.

TABLE 11

Summary of 5T4 Tissue Distribution

| | [1]Donors | | | |
|---|---|---|---|---|
| Tissue | 1 | 2 | 3 | Staining Distribution |
| Adrenal | − | − | − | |
| Bladder | +/++ | − | − | Urothelium only stained (Nt and 1:8) |
| Blood Cells | | | | |
| Bone Marrow | | | | |
| Breast | − | − | − | |
| Brain Cerebellum | − | − | − | |
| Brain Cortex | − | − | − | |
| Colon | − | − | − | |
| Endothelium | − | + | − | Variable staining in endothelium |
| Fallopian Tube | + | − | − | Variable staining of epithelium |
| Heart | − | − | − | |
| Kidney | − | − | − | |
| Liver | − | − | − | |
| Uterus Cervix | − | − | − | |
| [2]Uterus Endometrium | − | − | + | Epithelial cells positive |
| Lung | − | − | − | |
| Lymph Node | − | − | − | |

TABLE 11-continued

Summary of 5T4 Tissue Distribution

| Tissue | Donors[1] | | | Staining Distribution |
| --- | --- | --- | --- | --- |
| | 1 | 2 | 3 | |
| Ovary | + | – | – | Mesothelial and epithelial staining |
| Pancreas | – | – | – | |
| Parathyroid | – | – | – | |
| Pituitary | + | – | + | Individual cells staining |
| Placenta | +++ | +++ | +++ | All staining on trophoblasts surface |
| Prostate | – | – | – | |
| Skin | – | – | – | |
| Spinal Cord | – | – | – | |
| Spleen | – | – | – | |
| Striated Muscle | – | – | – | |
| Testis | – | – | – | |
| Thymus | | | | |
| Thyroid | – | – | – | |
| Ureter[2] | + | + | + | Urothelium only stained (Nt and 1:8) |
| Gastric Antrum | – | – | – | |
| Gastric Body | – | – | – | |
| Ileum | – | – | – | |
| Duodenum[2] | ++/+ | – | + | Muscularis mucosa only stained |
| Eye Cornea | – | – | – | |
| Eye Lens | – | – | – | |
| Eye Retina | – | – | – | |

[1]5T4 staining intensity was defined by visual analysis relative to placenta trophoblasts (+++) and negative control staining (–).
[2]Tissues derived from cancer patients Example 13

ScFv Fusion Protein In Vivo Anti Tumour Efficacy Data

The purpose of the study was to test the efficacy of a series of single chain antibody fusion proteins.

Experimental Design

CT26 cells expressing human 5T4 (CT26-h5T4) and CT26-neo

Cells were pre-incubated with:
PBS, LscFv-1, LscFv-2, B7-scFv, ScFv-Ig

LscFv-1 and 2 were expressed in a BHK cell line. LscFv-1 was purified via its Histidine tag on a Nickel column and scFv-2 was purified using a filtration system. B7-scFv was purified from a BHK line via a His tag and scFv-Ig was purified via a filtration column. The concentration of each scFv used in the experiment was defined as the amount of protein required to saturate binding of CT26-h5T4 cells in a FACS assay.

CT26-h5T4 and CT26-neo cells were pre-incubated with saturating amounts of each scFv and incubated for 1 hour. After washing cells $5\times10^5$ cells were injected subcutaneously into the flanks of syngeneic BALB/c mice.

Tumour measurements were taken every two days and the volume calculated.

Results 13

FIG. 8: CT26-neo

There is not a significant difference between the groups accept in the case of LscFv-1, for which appears to be 3-fold reduction in tumour size compared to the PBS control 36 days after tumour inoculation.

FIG. 9: CT26-h5T4

Tumours treated with all the scFv constructs had a significant effect on tumour growth. 4 of the 5 mice treated with scFv-1 were tumour free on day 36. On day 36 scFv-1 treated tumour were >60 fold smaller than tumours treated with PBS.

When a similar experiment was carried out using a mouse melanoma line (B16) engineered to express h5T4 there was no anti-tumour effect.

Summary

In summary there appears to be no benefit of fusing B7 or IgG to the 5T4 specific scFv in the CT26 and B16 murine models. The scFv alone may be more efficacious due to its higher binding affinity (as shown in BIACORE compared to B7-scFV). Thefore this data indicates that the scFv alone has a significant effect on tumour retardation and immune enhancing molecules fused to the scFv may not be required to show an effect on tumour retardation in the 5T4 model.

The invention claimed is:

1. A pharmaceutical composition comprising a non-human, mammalian 5T4 antigen and a pharmaceutically acceptable carrier wherein administration of the composition to a mammalian subject induces an anti-tumor immunotherapeutic response.

2. The composition according to claim 1, further comprising one or more adjuvants.

3. The composition according to claim 1, wherein the 5T4 antigen is modified to differ from a naturally occurring mammalian 5T4 antigen.

4. The composition according to claim 1, wherein the 5T4 antigen is modified to differ from a naturally occurring mammalian 5T4 antigen, and comprises a peptide epitope of a mammalian 5T4 antigen, and wherein the modified 5T4 antigen induces a CTL response.

5. The composition according to claim 1, wherein said non-human, mammalian 5T4 antigen is a murine antigen.

6. The composition according to claim 1, wherein said non-human, mammalian 5T4 antigen is a canine antigen.

7. An anti-tumor immunotherapeutic composition, comprising a 5T4 antigen modified to differ from a naturally occurring mammalian 5T4 antigen and a pharmaceutically acceptable carrier, wherein the modified 5T4 antigen comprises an HLA CTL peptide epitope of a mammalian 5T4 antigen and wherein administration of the composition to a mammalian subject induces an anti-tumor immunotherapeutic response.

8. The composition according to claim 7, wherein said naturally occurring mammalian 5T4 antigen is a human 5T4 antigen.

9. The composition according to claim 7, further comprising one or more adjuvants.

10. The composition according to claim 7, wherein said naturally occurring mammalian 5T4 antigen is a murine antigen.

11. The composition according to claim 7, wherein said naturally occurring mammalian 5T4 antigen is a canine antigen.

12. An isolated, non-human, mammalian 5T4 antigen.

13. The 5T4 antigen according to claim 12, wherein the antigen is modified to differ from a naturally occurring mammalian 5T4 antigen.

14. The 5T4 antigen according to claim 12, wherein the antigen is modified to differ from a naturally occurring mammalian 5T4 antigen, and comprises a peptide epitope of a mammalian 5T4 antigen, and wherein the modified 5T4 antigen induces a CTL response.

15. An isolated, non-human, mammalian 5T4 antigen, wherein said antigen is a murine antigen.

16. An isolated, non-human, mammalian 5T4 antigen, wherein said antigen is a canine antigen.

\* \* \* \* \*

SEQUENCE LISTING

```
<160> NUMBER OF SEQ ID NOS: 27

<210> SEQ ID NO 1
<211> LENGTH: 1263
<212> TYPE: DNA
<213> ORGANISM: Homo sapiens

<400> SEQUENCE: 1
atgcctgggg ggtgctcccg gggccccgcc gccggggacg ggcgtctgcg gctggcgcga       60
ctagcgctgg tactcctggg ctgggtctcc tcgtcttctc ccacctcctc ggcatcctcc      120
ttctcctcct cggcgccgtt cctggcttcc gccgtgtccg cccagccccc gctgccggac      180
cagtgccccg cgctgtgcga gtgctccgag gcagcgcgca cagtcaagtg cgttaaccgc      240
aatctgaccg aggtgcccac ggacctgccc gcctacgtgc gcaacctctt ccttaccggc      300
aaccagctgg ccgtgctccc tgccggcgcc ttcgcccgcc ggccgccgct ggcggagctg      360
gccgcgctca acctcagcgg cagccgcctg gacgaggtgc gcgcgggcgc cttcgagcat      420
ctgcccagcc tgcgccagct cgacctcagc cacaacccac tggccgacct cagtcccttc      480
```

-continued

```
gctttctcgg gcagcaatgc cagcgtctcg gcccccagtc cccttgtgga actgatcctg      540
aaccacatcg tgcccctga agatgagcgg cagaaccgga gcttcgaggg catggtggtg      600
gcggccctgc tggcgggccg tgcactgcag gggctccgcc gcttggagct ggccagcaac      660
cacttccttt acctgccgcg ggatgtgctg gcccaactgc ccagcctcag gcacctggac      720
ttaagtaata attcgctggt gagcctgacc tacgtgtcct tccgcaacct gacacatcta      780
gaaagcctcc acctggagga caatgccctc aaggtccttc acaatggcac cctggctgag      840
ttgcaaggtc taccccacat tagggttttc ctggacaaca atccctgggt ctgcgactgc      900
cacatggcag acatggtgac ctggctcaag gaaacagagg tagtgcaggg caaagaccgg      960
ctcacctgtg catatccgga aaaaatgagg aatcgggtcc tcttggaact caacagtgct     1020
gacctggact gtgacccgat tcttccccca tccctgcaaa cctcttatgt cttcctgggt     1080
attgttttag ccctgatagg cgctattttc ctcctggttt tgtatttgaa ccgcaagggg     1140 ataaaaagt ggatgcataa catcagagat gcctgcaggg atcacatgga agggtatcat      1200
tacagatatg aaatcaatgc ggaccccaga ttaacaaacc tcagttctaa ctcggatgtc     1260
tga                                                                   1263
```

<210> SEQ ID NO 2
<211> LENGTH: 1281
<212> TYPE: DNA
<213> ORGANISM: Mus musculus

<400> SEQUENCE: 2

```
atgcctgggg cgggctcccg gggcccctcc gccggggacg gacggctgag gttggcaagg      60
ctggcgctag tgctgctggg ttgggtctcc gcgtcggccc ccagctcttc ggtaccctcg     120
tcttccacct ccccggcaga cttcctggcc tcggggtctg cgcagcctcc gccagccgag     180
agatgccccg cggcgtgcga gtgctccgag gcggcgcgca cggttaagtg cgtgaaccgc     240
aacctgctgg aggtgccggc ggatctaccg ccttacgtgc gcaaccttt ccttaccggc      300 aaccagatga ccgtgctccc cgcgggcgcc ttcgcccgcc agccgccgct cgccgacctg     360
gaggcgctca acctcagcgg caaccacctg aaggaggtgt gtgcaggtgc cttcgagcat     420
ctgccgggtc tgcgccggct tgacctcagc acaacccctc tcaccaacct cagcgccttc     480
gtctttgcgg gcagcaacgc cagcgtctcg gcccccagcc cctggagga gctgatcctg      540 aatcacatcg tgcccctga ggatcagagg cagaacggga gcttcgaggg tatggtggcc      600
ttcgaaggca tggtggcagc agctctgcgc tcaggccttg cactccgagg tcttacacgc     660
ctggagctag ccagcaatca ctttcttttc ctgcctcggg acttactagc ccaactgccg     720
agtctcagat acctggacct caggaacaat tccctggtga cctgaccta cgcatccttc      780 cgcaacctga cacacctcga aagcctccac ttggaggaca atgccctcaa ggtccttcac     840
aactccacct tggctgagtg gcaaggcctg gctcatgtca aggtgttcct ggacaacaat      900
ccctgggttt gcgactgcta catggctgac atggtggctt ggcttaaaga gacagaggtg      960
gtgccagata aagccaggct tacctgcgca ttccgggaga gatgaggaa tcgtggcctc     1020 ttagacctca acagctctga cctggactgt gacgctgtcc ttccccaatc cctgcagact     1080
tcctatgtct tcctaggtat tgttttagct ctgataggcg ctattttcct cctcgttttg     1140
tatttgaacc gtaaaggcat aaaaagtgg atgcataaca tcagagatgc ctgcagggat      1200
cacatggaag ggtatcatta cagatacgaa atcaatgcgg accccagatt aacaaatctt     1260
agttccaact cggatgtctg a                                               1281
```

<210> SEQ ID NO 3
<211> LENGTH: 901
<212> TYPE: DNA
<213> ORGANISM: Canis sp.
<220> FEATURE:
<221> NAME/KEY: modified_base
<222> LOCATION: (66)
<223> OTHER INFORMATION: a, c, g or t
<220> FEATURE:
<221> NAME/KEY: modified_base
<222> LOCATION: (145)
<223> OTHER INFORMATION: a, c, g or t
<220> FEATURE:
<221> NAME/KEY: modified_base
<222> LOCATION: (277)..(278)
<223> OTHER INFORMATION: a, c, g or t
<220> FEATURE:
<221> NAME/KEY: modified_base
<222> LOCATION: (287)
<223> OTHER INFORMATION: a, c, g or t
<220> FEATURE:
<221> NAME/KEY: modified_base
<222> LOCATION: (353)
<223> OTHER INFORMATION: a, c, g or t
<220> FEATURE:
<221> NAME/KEY: modified_base
<222> LOCATION: (358)
<223> OTHER INFORMATION: a, c, g or t
<220> FEATURE:
<221> NAME/KEY: modified_base
<222> LOCATION: (428)..(429)
<223> OTHER INFORMATION: a, c, g or t
<220> FEATURE:
<221> NAME/KEY: modified_base
<222> LOCATION: (577)
<223> OTHER INFORMATION: a, c, g or t
<220> FEATURE:
<221> NAME/KEY: modified_base
<222> LOCATION: (580)
<223> OTHER INFORMATION: a, c, g or t
<220> FEATURE:
<221> NAME/KEY: modified_base
<222> LOCATION: (719)
<223> OTHER INFORMATION: a, c, g or t
<220> FEATURE:
<221> NAME/KEY: modified_base
<222> LOCATION: (788)
<223> OTHER INFORMATION: a, c, g or t
<220> FEATURE:
<221> NAME/KEY: modified_base
<222> LOCATION: (863)
<223> OTHER INFORMATION: a, c, g or t
<220> FEATURE:
<221> NAME/KEY: modified_base
<222> LOCATION: (868)
<223> OTHER INFORMATION: a, c, g or t
<220> FEATURE:
<221> NAME/KEY: modified_base
<222> LOCATION: (871)
<223> OTHER INFORMATION: a, c, g or t

<400> SEQUENCE: 3

```
atcgtgcccc ccgacgaccg gcggcagaac cggagcttcg aggtcatggt ggcggctgcc      60
vddrrnrsvm vaaactccga gcgggccgcg cgcttcgcgg gctgcagtgc ctggagctgg     120
ccggcaaccg cttcragrar gcagnrctct acttgcctcg cgacgtcctg gcccagctac    180
ccggcctccg gcacctggac ctgcgcyrdv agrhdraaca attccctggt gagcctcacc    240
tacgtgtcct tccgcaacct gacgcacttg gagagcnnsv styvsrnths ctccacctgg    300
aggacaacgc cctcaaggtc cttcacaacg ccaccctggc ggagctgcag hdnakvhnat    360
aagcctgccc cacgtccggg tcttcctgga caacaacccc tgggtctgcg attgtcacat    420
```

```
gshvrvdnnw vcdchmgcag acatggtggc ctggctcaag gagacagagg tggtgccggg    480
caaagccggg ctcaccadmv awktvvgkag ttgtgcattc ccggagaaaa tgaggaatcg    540
ggccctcttg gaactcaaca gctcccacct gcakmrnran sshgactgtg accctatcct   600
ccctccatcc ctgcagactt cttatgtctt cctaggtatt gtcdcdstsy vgvttagccc    660
tgataggcgc catcttccta ctggttttgt atttgaaccg caaggggata aagagavynr    720
kgkaagtgga tgcataacat cagagatgcc tgcagggatc acatggaagg gtatcactac    780
agakwmhnrd acrdhmgyhy rtacgaaatc aatgcagacc ccaggttaac aaacctcagt    840
tccaattcgg atgtctgaga aynadrtnss nsdvacagtc ggggacagac caaggacaac    900
t                                                                   901
```

<210> SEQ ID NO 4
<211> LENGTH: 238
<212> TYPE: PRT
<213> ORGANISM: Canis sp.

<400> SEQUENCE: 4

```
Ile Val Pro Pro Asp Asp Arg Arg Gln Asn Arg Ser Phe Glu Val Met
 1               5                  10                  15

Val Ala Ala Ala Leu Arg Ala Gly Arg Ala Leu Arg Gly Leu Gln Cys
             20                  25                  30

Leu Glu Leu Ala Gly Asn Arg Phe Leu Tyr Leu Pro Arg Asp Val Leu
         35                  40                  45

Ala Gln Leu Pro Gly Leu Arg His Leu Asp Leu Arg Asn Asn Ser Leu
     50                  55                  60

Val Ser Leu Thr Tyr Val Ser Phe Arg Asn Leu Thr His Leu Glu Ser
 65                  70                  75                  80

Leu His Leu Glu Asp Asn Ala Leu Lys Val Leu His Asn Ala Thr Leu
                 85                  90                  95

Ala Glu Leu Gln Ser Leu Pro His Val Arg Val Phe Leu Asp Asn Asn
            100                 105                 110

Pro Trp Val Cys Asp Cys His Met Ala Asp Met Val Ala Trp Leu Lys
        115                 120                 125

Glu Thr Glu Val Val Pro Gly Lys Ala Gly Leu Thr Cys Ala Phe Pro
    130                 135                 140

Glu Lys Met Arg Asn Arg Ala Leu Leu Glu Leu Asn Ser Ser His Leu
145                 150                 155                 160

Asp Cys Asp Pro Ile Leu Pro Pro Ser Leu Gln Thr Ser Tyr Val Phe
                165                 170                 175

Leu Gly Ile Val Leu Ala Leu Ile Gly Ala Ile Phe Leu Leu Val Leu
            180                 185                 190

Tyr Leu Asn Arg Lys Gly Ile Lys Lys Trp Met His Asn Ile Arg Asp
        195                 200                 205

Ala Cys Arg Asp His Met Glu Gly Tyr His Tyr Arg Tyr Glu Ile Asn
    210                 215                 220

Ala Asp Pro Arg Leu Thr Asn Leu Ser Ser Asn Ser Asp Val
225                 230                 235
```

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: 5T4 9 Mer -continued

```
<400> SEQUENCE: 5

Phe Leu Thr Gly Asn Gln Leu Ala Val
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: 5T4 9 Mer

<400> SEQUENCE: 6

Ala Leu Ile Gly Ala Ile Phe Leu Leu
1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: 5T4 9 Mer

<400> SEQUENCE: 7

Ser Leu Gln Thr Ser Tyr Val Phe Leu
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: 5T4 9 Mer

<400> SEQUENCE: 8

Ala Ile Phe Leu Leu Val Leu Tyr Leu
1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: 5T4 9 Mer

<400> SEQUENCE: 9

Gly Leu Pro His Ile Arg Val Phe Leu
1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: 5T4 9 Mer

<400> SEQUENCE: 10

Phe Leu Gly Ile Val Leu Ala Leu Ile
1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: 5T4 9 Mer

<400> SEQUENCE: 11
```

```
Asn Leu Thr Glu Val Pro Thr Asp Leu
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: 5T4 9 Mer

<400> SEQUENCE: 12

Asn Leu Phe Leu Thr Gly Asn Gln Leu
1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: 5T4 9 Mer

<400> SEQUENCE: 13

Phe Leu Tyr Leu Pro Arg Asp Val Leu
1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: 5T4 9 Mer

<400> SEQUENCE: 14

Val Leu Tyr Leu Asn Arg Lys Gly Ile
1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: 5T4 9 Mer

<400> SEQUENCE: 15

Leu Ile Gly Ala Ile Phe Leu Leu Val
1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: 5T4 9 Mer

<400> SEQUENCE: 16

Phe Leu Asp Asn Asn Pro Trp Val Cys
1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: 5T4 9 Mer

<400> SEQUENCE: 17
```

```
His Met Ala Asp Met Val Thr Trp Leu
1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: 5T4 9 Mer

<400> SEQUENCE: 18

Tyr Met Ala Asp Met Val Ala Trp Leu
1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: 5T4 9 Mer

<400> SEQUENCE: 19

Asn Leu Leu Glu Val Pro Ala Asp Leu
1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: 5T4 9 Mer

<400> SEQUENCE: 20

Phe Leu Thr Gly Asn Gln Met Thr Val
1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: 5T4 9 Mer

<400> SEQUENCE: 21

Ala Leu Ile Gly Ala Ile Phe Leu Leu
1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: 5T4 9 Mer

<400> SEQUENCE: 22

Phe Leu Phe Leu Pro Arg Asp Leu Leu
1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: 5T4 9 Mer

<400> SEQUENCE: 23

Ser Leu Gln Thr Ser Tyr Val Phe Leu
```

```
<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: 5T4 9 Mer

<400> SEQUENCE: 24

Ala Ile Phe Leu Leu Val Leu Tyr Leu
1               5

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: 5T4 9 Mer

<400> SEQUENCE: 25

Gly Leu Ala His Val Lys Val Phe Leu
1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: 5T4 9 Mer

<400> SEQUENCE: 26

Phe Leu Gly Ile Val Leu Ala Leu Ile
1               5

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence: 5T4 9 Mer

<400> SEQUENCE: 27

Val Leu Tyr Leu Asn Arg Lys Gly
1               5
```